United States Patent
O'Neill et al.

(10) Patent No.: US 10,460,929 B2
(45) Date of Patent: *Oct. 29, 2019

(54) ORGANOAMINOSILANE PRECURSORS AND METHODS FOR DEPOSITING FILMS COMPRISING SAME

(71) Applicant: Versum Materials US, LLC, Allentown, PA (US)

(72) Inventors: Mark Leonard O'Neill, Queen Creek, AZ (US); Manchao Xiao, San Diego, CA (US); Xinjian Lei, Vista, CA (US); Richard Ho, Anaheim, CA (US); Haripin Chandra, San Marcos, CA (US); Matthew R. MacDonald, Laguna Niguel, CA (US); Meiliang Wang, San Marcos, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/479,893

(22) Filed: Apr. 5, 2017

(65) Prior Publication Data

US 2017/0207084 A1 Jul. 20, 2017

Related U.S. Application Data

(63) Continuation of application No. 14/483,751, filed on Sep. 11, 2014.
(Continued)

(51) Int. Cl.
*H01L 21/02* (2006.01)
*C07F 7/10* (2006.01)
(Continued)

(52) U.S. Cl.
CPC .......... *H01L 21/02219* (2013.01); *C07F 7/10* (2013.01); *C09D 5/24* (2013.01); *C23C 16/24* (2013.01); *C23C 16/45553* (2013.01); *H01L 21/0214* (2013.01); *H01L 21/0217* (2013.01); *H01L 21/0228* (2013.01); *H01L 21/0262* (2013.01); *H01L 21/02126* (2013.01);
(Continued)

(58) Field of Classification Search
CPC ........... H01L 21/02219; H01L 21/0214; H01L 21/02164
See application file for complete search history.

(56) References Cited

U.S. PATENT DOCUMENTS 5,622,784 A 4/1997 Okaue et al.
7,125,582 B2 10/2006 McSwiney et al.
(Continued)

FOREIGN PATENT DOCUMENTS

CN 102247821 11/2011
EP 1 724 373 A1 11/2006
(Continued)

OTHER PUBLICATIONS

RN 5626-01-7 (Entered STN Nov. 16, 1984).*
(Continued)

*Primary Examiner* — Pancham Bakshi
(74) *Attorney, Agent, or Firm* — Michael K. Boyer; David K. Benson

(57) ABSTRACT

Described herein are precursors and methods for forming silicon-containing films. In one aspect, the precursor comprises a compound represented by one of following Formulae A through E below:

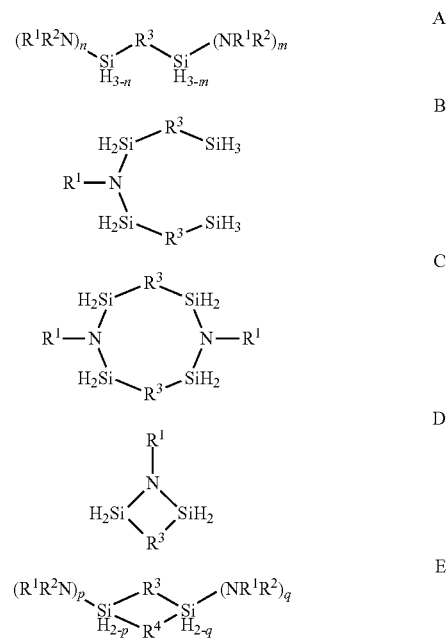

In one particular embodiment, the organoaminosilane precursors are effective for a low temperature (e.g., 350° C. or less), atomic layer deposition (ALD) or plasma enhanced atomic layer deposition (PEALD) of a silicon-containing film. In addition, described herein is a composition comprising an organoaminosilane described herein wherein the organoaminosilane is substantially free of at least one selected from the amines, halides (e.g., Cl, F, I, Br), higher molecular weight species, and trace metals.

5 Claims, 1 Drawing Sheet

Related U.S. Application Data

(60) Provisional application No. 61/880,261, filed on Sep. 20, 2013.

(51) Int. Cl.
  *C23C 16/24* (2006.01)
  *C23C 16/455* (2006.01)
  *C09D 5/24* (2006.01)

(52) U.S. Cl.
  CPC .. *H01L 21/02164* (2013.01); *H01L 21/02167* (2013.01); *H01L 21/02211* (2013.01); *H01L 21/02271* (2013.01); *H01L 21/02274* (2013.01); *H01L 21/02532* (2013.01); *H01L 21/02592* (2013.01); *H01L 21/02598* (2013.01)

(56) References Cited

U.S. PATENT DOCUMENTS

| | | | | |
|---|---|---|---|---|
| 7,875,312 | B2 * | 1/2011 | Thridandam | C23C 16/402 427/248.1 |
| 2012/0003500 | A1 | 1/2012 | Yoshida et al. | |
| 2012/0128897 | A1 | 5/2012 | Xiao et al. | |
| 2013/0224964 | A1 | 8/2013 | Fukazawa et al. | |
| 2015/0147871 | A1 | 5/2015 | Xiao | |

FOREIGN PATENT DOCUMENTS

| | | |
|---|---|---|
| JP | 4196246 | 7/1992 |
| JP | 2002158223 | 5/2002 |
| JP | 2003151972 | 5/2003 |
| JP | 201225773 | 2/2012 |
| KR | 20130034001 | 4/2013 |
| TW | 201114941 | 5/2011 |
| TW | 201319077 | 5/2013 |
| WO | 2009058732 | 5/2009 |
| WO | 2014201033 | 12/2014 |
| WO | 2016007708 | 1/2016 |

OTHER PUBLICATIONS

Norbert W. Mitzel, et al, "Synthesis of Volatile Cyclic Silylamines and the Molecular Structures of Two 1-Aza-2,5-disilacyclopentane Derivatives", Inorg. Chem., 1997, 4360-4368.

Hubert Schmidbaur, et al, "Diffrences in Reactivity of 1,4-Disilabutane and n-Tetrasilane towards Secondary Amines", Anorganisch-chemisches Institut der Technischen Universitat Munchen, 1990, 1679-1683.

I. Suzuki, et al, "Extra Low-temperature SiO2 Deposition Using Aminosilanes", ECS Transactions, 2007, 119-128.

Mark L. O'Neill, et al, "Impact of Aminosilane Precursor Structure on Silicon Oxides by Atomic Layer Deposition", The Electrochemical Society, Winter 2011, 33-37.

Seok-Jun Won, et al, "Growth and electrical properties of silicon oxide grown by atomic layer deposition using Bis (ethyl-methyl-amino)silane and ozone", J. Vac. Sci. Technol., 2012, 01A126-1-01A126-7.

Lei Han, et al, "High-Quality Thin SiO2 Films Grown by Atomic Layer Deposition Using Tris(dimethylamino)silane (TDMAS) and Ozone", ECS Journal of Solid State Science and Technology, 2013, N228-N236.

Han Zhou, et al, "Highly Stable Ultrathin Carbosiloxane Films by Molecular Layer Deposition", The Journal of Physical Chemistry, 2013, 19967-19973.

Anu Mallikarjunan, et al, "Designing High Performance Precursors for Atmoic Layer Deposition of Silicon Oxide", Air Products and Chemicals, Inc., 199.

Chiara, J. L., "N-silylarylamines", Chemical Abstracts Service, Columbus, Ohio, US, 2007, XP002762594, retrieved from STN, Database accession No. 2007:1251060 Abstract.

Kuntsmann, Th., et al., "Novel brominated carbosilane precursors for low-temperature heteroepitaxy of .beta.-SiC and their comparison with methyltrichlorosilane", Chemistry of Materials, vol. 7, No. 9, 1995, pp. 1675-1679.

Wendt, H., et al., "Formation of organosilicon compounds. 116. The influence of chlorination, hydrogenation and crosslinking on the thermal behavior of the polymeric (-Me2Si-Ch2-)n", Chemical Abstracts Service, Columbus, Ohio, US, 2007, XP002766905, retrieved from STN, Database accession No. 1997:298219 "Abstract".

Lienhard, K., et al., "Aminosilanes and silazanes with the Si-Ch2-Si grouping", Chemical Abstracts Service, Columbus, Ohio, US, 2007, XP002766906, retrieved from STN, Database accession No. 1963:482331 "Abstract".

Mitzel, Norbert W., et al., "Cyclic Silylhydrazines and Their Borane Adducts", 1995 American Chemical Society, Inorg. Chem. 1995, 34, pp. 4840-4845.

Mitzel, Norbert W., et al., "Two Different Cyclization Modes in the Formation of Silylhydrazines", 1993 American Chemical Society, Organometallics 1993, 12, pp. 413-416.

RN: 51058-37-8 Registry, STN: Nov. 16, 1984.

Robert Schrock, et al., "Disiloxanes, Disilazanes and Related Compounds Derived from 1,8-Disilylnaphthalene", Chemische Berichte, 1996, 495-501.

Registry STN, Nov. 16, 1984, RN:5649-53-6.

Registry STN, Nov. 16, 1984, RN:5626-01-7.

R. Schrock, et al, "Cyclic and open-chain derivatives of bis(trihydrosilyl)benzenes", J. Chem. Soc., 1996, 4193-4196.

W. Uhlig, "Functionalization and Cross-Linking of Poly(silylenmethylenes)", Zeitschrift fur Naturforschung, 1997, 577-586.

N. Auner, et al, "Silaethane II: Darstellung und Charakterisierung von 1,3-Disilacyclobutanen", Journal of Organometallic Chemistry, 1980, 151-177.

N. Auner, et al, "Silaheterocyclen IX. Darstellung und Charakterisierung von 2,4-Dineopentyl-1,3-disilacyclobutanen", Journal of Organometallic Chemistry, 1990, 33-56.

S. Papetti, et al, "A New Series of Organoboranes. V. Some Chemstry of Cyclic Silyl Carboranes", Inorganic Chemistry, 1964, 1444-1447.

* cited by examiner

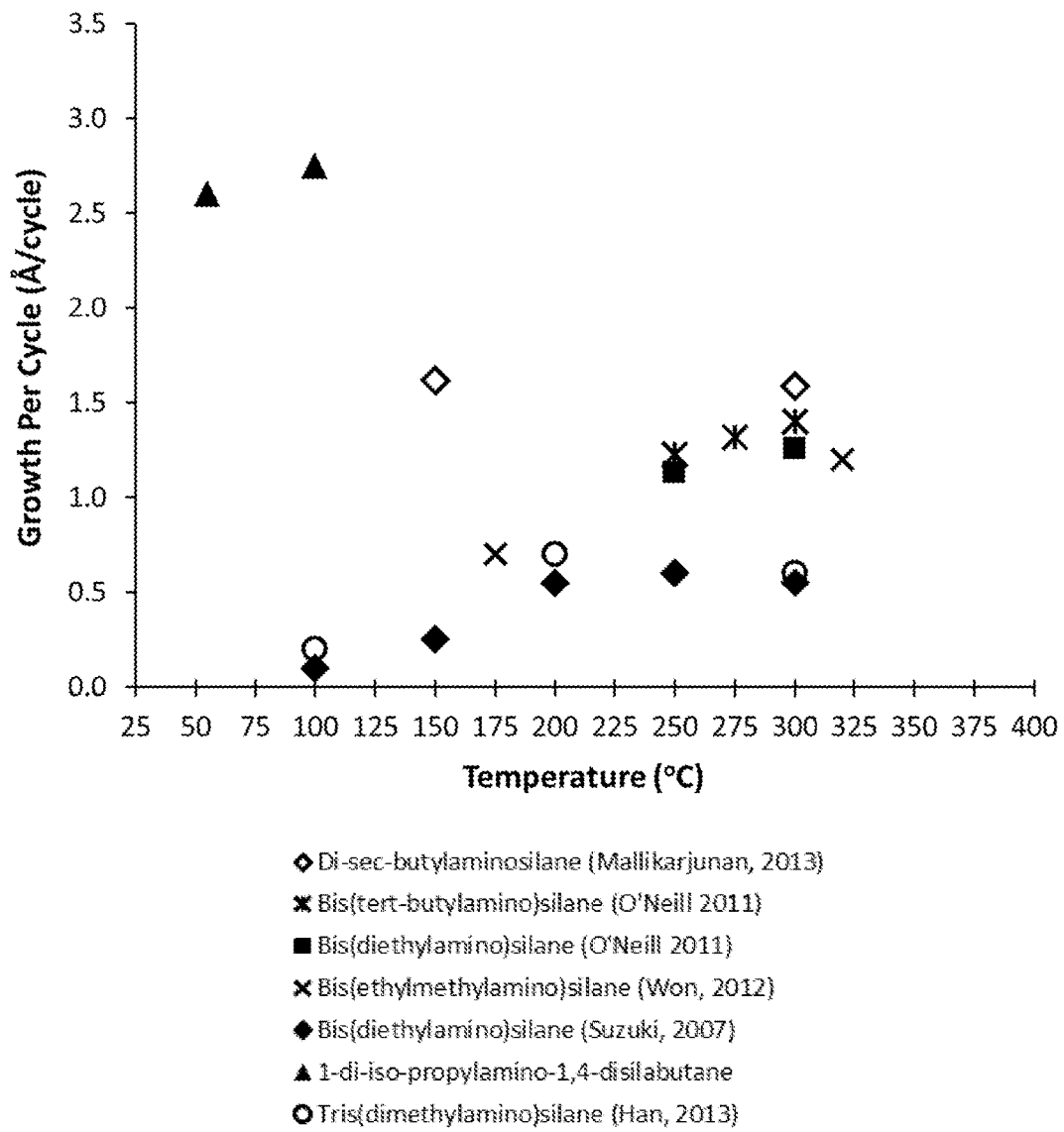

ORGANOAMINOSILANE PRECURSORS AND METHODS FOR DEPOSITING FILMS COMPRISING SAME

CROSS-REFERENCE TO RELATED APPLICATIONS

This application is a continuation of application Ser. No. 14/483,751, filed on Sep. 11, 2014. This application also claims the priority benefit of U.S. Provisional Application No. 61/880,261, filed Sep. 20, 2013. The disclosure of this provisional application is hereby incorporated by reference in its entirety.

BACKGROUND OF THE INVENTION

Precursors, particularly organoaminosilane, and compositions thereof that can be used for the deposition of silicon-containing films, including but not limited to, amorphous silicon, crystalline silicon, silicon nitride, silicon oxide, carbon doped silicon oxide, silicon carbo-nitride, and silicon oxynitride films are described herein. In yet another aspect, described herein is the use of the precursors for depositing silicon-containing films in the fabrication of integrated circuit devices. In these or other aspects, the organoaminosilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Several classes of compounds can be used as precursors for silicon-containing films such as, but not limited to, silicon oxide, carbon doped silicon oxide or silicon nitride films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Low pressure chemical vapor deposition (LPCVD) processes are one of the more widely accepted methods used by semiconductor industry for the deposition of silicon-containing films. Low pressure chemical vapor deposition (LP-CVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Precursors that are used in depositing silicon nitride films such as BTBAS and chlorosilanes generally deposit the films at temperatures greater than 550° C. The trend of miniaturization of semiconductor devices and low thermal budget requires a lower process temperature and a higher deposition rate. The temperature, at which the silicon films are deposited, should decrease in order to prevent ion diffusion in the lattice, particularly for those substrates comprising metallization layers and on many Group III-V and II-VI devices. Accordingly, there is a need in the art to provide precursors for the deposition of silicon-containing films, such as silicon oxide, carbon doped silicon oxide, silicon oxynitride, or silicon nitride films that are sufficiently chemically reactive to allow deposition via CVD, ALD or other processes at temperatures of 550° C. or below or even at room temperature.

US Publ. No. 2013/224964 describes a method of forming a dielectric film having Si—C bonds on a semiconductor substrate by atomic layer deposition (ALD), includes: (i) adsorbing a precursor on a surface of a substrate; (ii) reacting the adsorbed precursor and a reactant gas on the surface; and (iii) repeating steps (i) and (ii) to form a dielectric film having at least Si—C bonds on the substrate. The precursor has a Si—C—Si bond in its molecule, and the reactant gas is oxygen-free and halogen-free and is constituted by at least a rare gas.

JP Pat. No. JP2002158223 describes insulator films that are formed using Si-type materials with the formula: $\{R^3(R^4)N\}_3Si-\{C(R^1)R^2\}_n-Si\{N(R^5)R^6\}_3$, where $R^1$, $R^2$=H, hydrocarbon groups, or X (halogen atom)-substituted hydrocarbon groups ($R^1$ and $R^2$ can be same), n=1-5 integer, $R^3$, $R^4$, $R^4$ and $R^6$=H, hydrocarbon groups or X (halogen atom)-substituted hydrocarbon groups ($R^3$, $R^4$, $R^5$ and $R^6$ can be same). The insulator films may be formed on substrates by CVD.

U.S. Pat. No. 7,125,582 describes a method and system that involves combining a Si source precursor and a nitrogen (N) source precursor at a temperature up to 550° C. and forming a Si nitride film.

The reference entitled "Synthesis of Volatile Cyclic Silylamines and the Molecular Structures of Two 1-Aza-2,5-disilacyclopentane Derivatives", Mitzel, N. W. et al., Inorg. Chem., Vol 36(20) (1997), pp. 4360-4368 describes a synthesis for making α,ω-bis(bromosilyl)alkanes, $BrH_2Si(CH_2)_n SiH_2Br$ (with n=2 and 3). In the reference, 1,2-Bis(bromosilyl)ethane reacts with ammonia to give 1,4-bis(1-aza-2,5-disilacyclopentane-1-yl)-1,4-disilabutane, traces of 1,6-diaza-2,5,7,10,11,14-hexasilabicyclo[4.4.4]tetradecane and nonvolatile products.

The reference entitled "Differences in reactivity of 1,4-disilabutane and n-tetrasilane towards secondary amines", Z. Naturforsch., B: Chem. Sci. FIELD Full Journal Title: Zeitschrift fuer Naturforschung, B: Chemical Sciences 45(12): 1679-83 described a synthesis for making aminosilanes using 1,4-Disilabutane $H_3SiCH_2CH_2SiH_3$ (I) and n-tetrasilane $H_3SiSiH_2SiH_2SiH_3$.

BRIEF SUMMARY OF THE INVENTION

Described herein are organoaminosilane precursors, compositions comprising same, and methods using same for forming films comprising silicon, such as, but not limited to, amorphous silicon, crystalline silicon, silicon oxide, carbon doped silicon oxide, silicon nitride, silicon oxynitride, silicon carbide, silicon carbonitride, and combinations thereof onto at least a portion of a substrate. In one particular embodiment, the organoaminosilane precursors are effective for a low temperature (e.g., 350° C. or less), atomic layer deposition (ALD) or plasma enhanced atomic layer deposition (PEALD) of silicon oxide or carbon doped silicon oxide films. In addition, described herein is a composition comprising an organoaminosilane described herein wherein the organoaminosilane is substantially free of at least one selected from the amines, halides (e.g., Cl, F, I, Br), higher molecular weight species, and trace metals. In these or other embodiments, the composition may further comprise a solvent. Also disclosed herein are methods to form films comprising silicon or coatings on an object to be processed, such as, for example, a semiconductor wafer. In one embodiment of the method described herein, a film comprising silicon and oxygen is deposited onto a substrate using an organoaminosilane precursor and an oxygen-containing source in a deposition chamber under conditions for generating a silicon oxide, carbon doped silicon oxide film on the substrate. In another embodiment of the method described herein, a film comprising silicon and nitrogen is deposited onto a substrate using an organoaminosilane precursor and a nitrogen containing precursor in a deposition chamber under conditions for generating a silicon nitride film on the substrate. In a further embodiment, the organoaminosilane precursors described herein can also be used a dopant for metal containing films, such as but not limited to, metal oxide films or metal nitride films. In the compositions and methods described herein, an organoaminosilane having the formula described herein is employed as at least one of the silicon containing precursors.

In one aspect, the organoaminosilane precursor described herein comprises a compound represented by one of following Formulae A through E below:

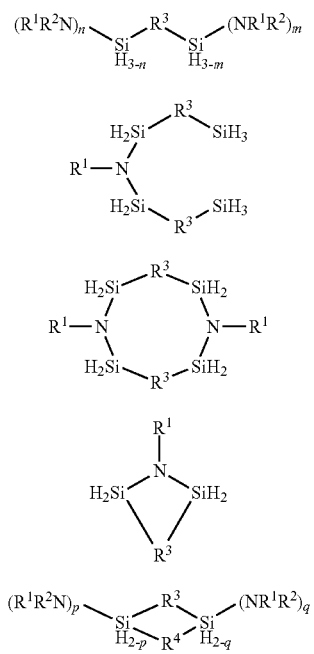

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3 and optionally wherein $R^3$ in Formula D forms a ring selected from a four-membered, five-membered or six-membered ring with the two silicon atoms and at least one nitrogen atom; and p and q in Formula E equal 1 or 2.

In another aspect, there is provided a composition comprising: (a) at least one organoaminosilane precursor a compound represented by one of following Formulae A through E below:

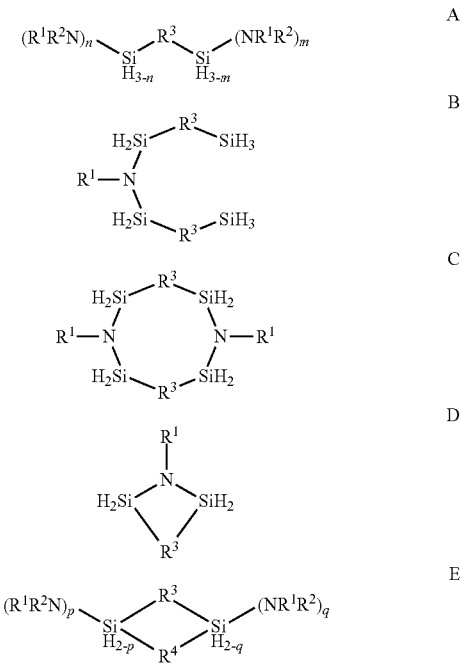

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and (b) a solvent. In certain embodiments of the composition described herein, exemplary solvents can include, without limitation, ether, tertiary amine, alkyl hydrocarbon, aromatic hydrocarbon, tertiary aminoether, and combinations thereof. In certain embodiments, the difference between the boiling point of the organoaminosilane and the boiling point of the solvent is 40° C. or less.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using at least one organoaminosilane precursor a compound represented by one of following Formulae A through E below:

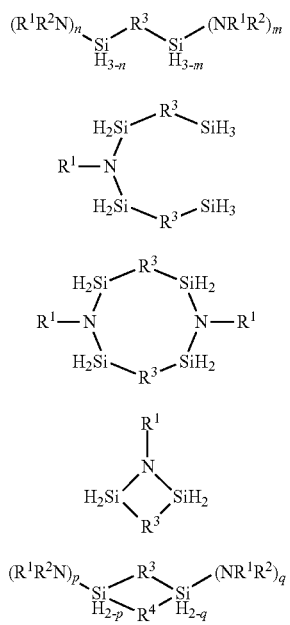

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom. In certain embodiments, $R^1$ and $R^2$ are the same. In other embodiments, $R^1$ and $R^2$ are different. In the foregoing or other embodiments, $R^1$ and $R^2$ can be linked together to form a ring. In further embodiments, $R^1$ and $R^2$ are not linked together to form a ring.

In another aspect, there is provided a method of forming a silicon oxide, carbon doped silicon oxide film via an atomic layer deposition process or ALD-like process, the method comprising the steps of:
 a. providing a substrate in a reactor;
 b. introducing into the reactor at least one organoaminosilane precursor a compound represented by one of following Formulae A through E below:

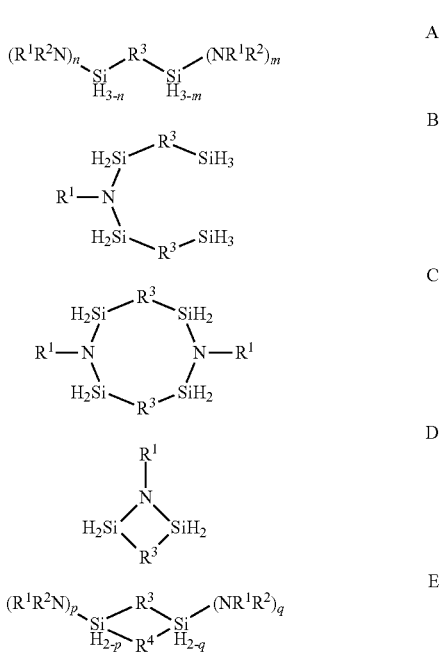

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;
 c. purging the reactor with a purge gas;
 d. introducing an oxygen-containing source into the reactor; and
 e. purging the reactor with a purge gas; wherein steps b through e are repeated until a desired thickness of the film is obtained.

In a further aspect, there is provided a method of forming a film selected from a silicon oxide film and a carbon doped silicon oxide film onto at least a surface of a substrate using a CVD process comprising:
 a. providing a substrate in a reactor;
 b. introducing into the reactor at least one organoaminosilane precursor a compound represented by one of following Formulae A through E below:

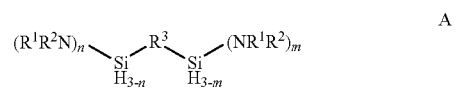

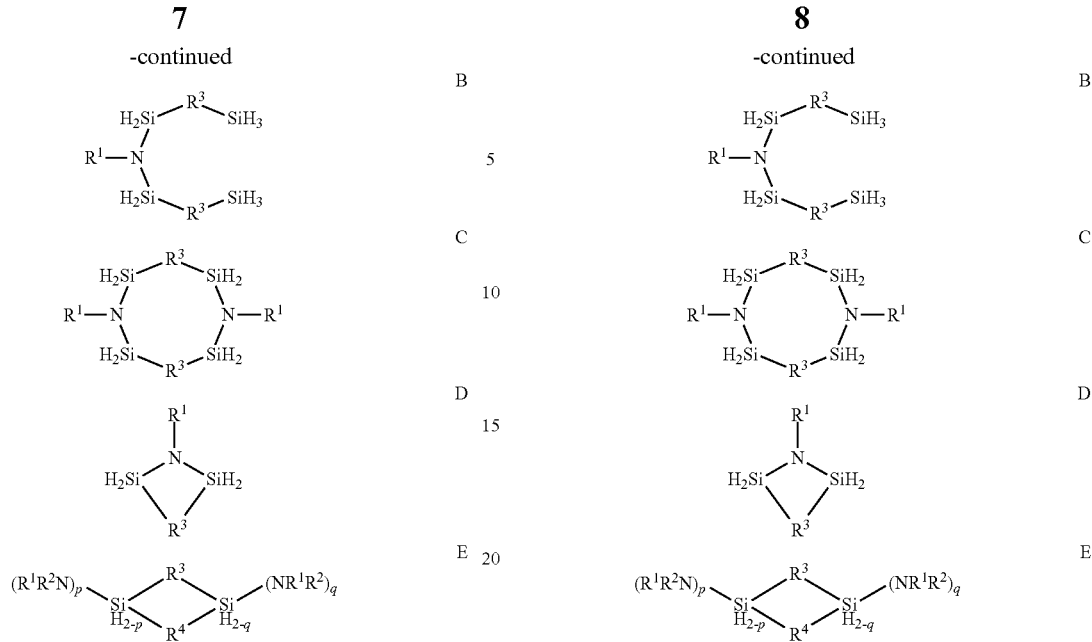

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and c. providing an oxygen-containing source to deposit the film onto the at least one surface. In certain embodiments of the method, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In another aspect, there is provided a method of forming a silicon nitride or silicon carbonitride film via an atomic layer deposition process, the method comprising the steps of:

a. providing a substrate in a reactor;

b. introducing into the reactor an at least one organoaminosilane precursor a compound represented by one of following Formulae A through E below:

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q equal 1 or 2 in Formula E and optionally wherein $R^3$ in Formula D forms a ring selected from a four-membered, five-membered or six-membered ring with the two silicon atoms and at least one nitrogen atom;

c. purging the reactor with a purge gas;

d. introducing a nitrogen-containing source into the reactor;

e. purging the reactor with a purge gas; and wherein steps b through e are repeated until a desired thickness of the silicon nitride film is obtained. In certain embodiments, $R^1$ and $R^2$ in Formulae A through E are the same. In other embodiments, $R^1$ and $R^2$ are different. In the foregoing or other embodiments, $R^1$ and $R^2$ can be linked together to form a ring. In a further embodiment, $R^1$ and $R^2$ are not linked together to form a ring.

In a further aspect, there is provided a method of forming a silicon nitride or carbonitride film onto at least a surface of a substrate using a CVD process comprising:

a. providing a substrate in a reactor;

b. introducing into the reactor at least one organoaminosilane precursor a compound represented by one of following Formulae A through E below:

-continued

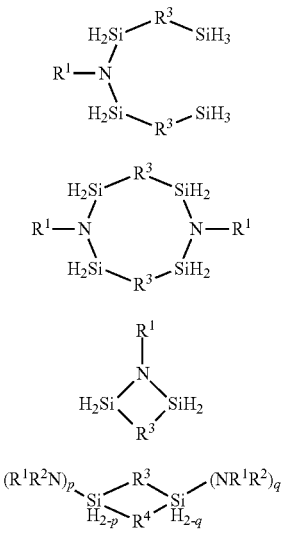

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;

c. providing a nitrogen-containing source wherein the at least one organoaminosilane precursors and the nitrogen-containing source react to deposit the film onto the at least one surface. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In a further embodiment of the method described herein, the process is depositing an amorphous or a crystalline silicon film. In this embodiment, the method comprises:

placing one or more substrates into a reactor which is heated to one or more temperatures ranging from ambient temperature to about 700° C.;

introducing at least one organoaminosilane precursor a compound represented by one of following Formulae A through E below:

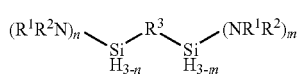 A

-continued

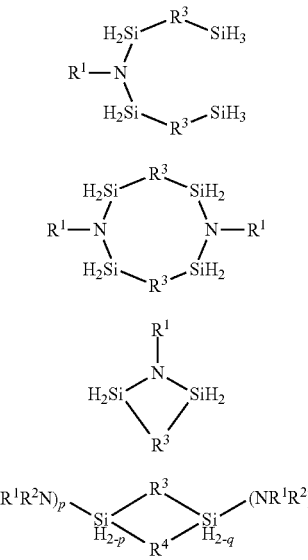

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and providing a reducing agent source into the reactor to at least partially react with the at least one organoaminosilane precursor and deposit a silicon-containing film onto the one or more substrates. The reducing agent is selected from the group consisting of hydrogen, hydrogen plasma, and hydrogen chloride. In certain embodiments of the CVD method, the reactor is maintained at a pressure ranging from 10 mTorr to 760 Torr during the introducing step. The above steps define one cycle for the method described herein, and the cycle of steps can be repeated until the desired thickness of a film is obtained. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In another aspect, there is provided a method of depositing an amorphous or a crystalline silicon film via an atomic layer deposition or cyclic chemical vapor deposition process, the method comprising the steps of:

a. providing a substrate in a reactor;

b. introducing into the reactor at least one organoaminosilane precursor a compound represented by one of following Formulae A through E below:

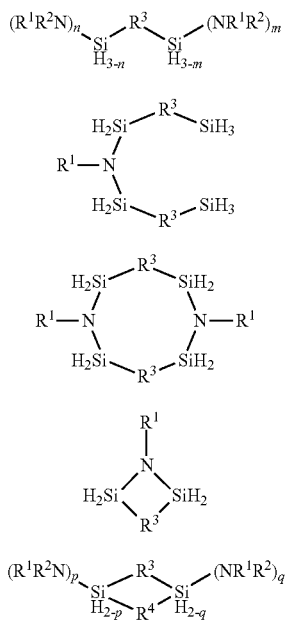

A

B

C

D

E

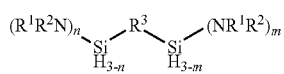

A wherein R¹ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein R² is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, R³ and R⁴ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein R³ in Formula D forms a ring selected from a four-membered, five-membered or six-membered ring with the two silicon atoms and at least one nitrogen atom wherein step b is repeated until a desired thickness of the film is obtained. In certain embodiments, the thickness of the film can be 1 Å or greater, or 1 to 10,000 Å, or 1 to 1000 Å, or 1 to 100 Å.

In another aspect, a vessel for depositing a silicon-containing film comprising one or more organoaminosilane precursor having any one of Formulae A, B, C, or D or E a combination thereof of one or more precursors represented by Formulae A, B, C, D or E is described herein. In one particular embodiment, the vessel comprises at least one pressurizable vessel (preferably of stainless steel) fitted with the proper valves and fittings to allow the delivery of one or more precursors to the reactor for a CVD or an ALD process.

In yet another aspect, there is provided a method for preparing an organoaminosilane comprising a compound represented by one of following Formulae A through E below:

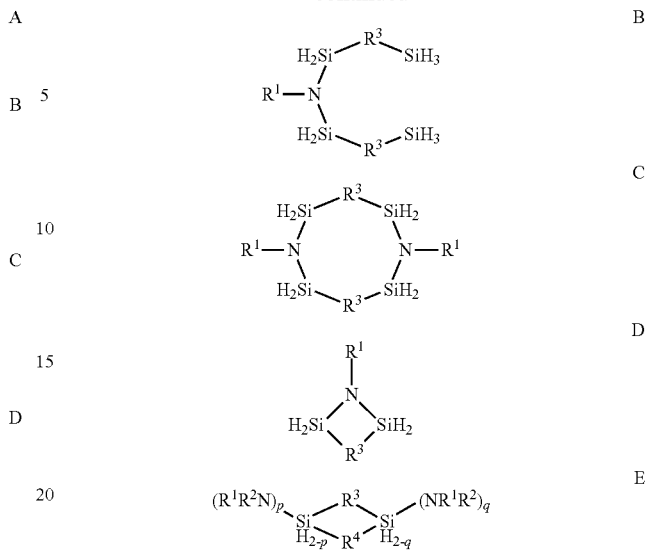

B

C

D

E wherein R¹ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein R² is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, R³ and R⁴ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; wherein n in Formula A equals 1 or 2; m in Formula A equals 0, 1, 2, or 3; p and q equal 1 or 2 in Formula E and optionally wherein R³ in Formula D forms a ring selected from a four-membered, five-membered or six-membered ring with the two silicon atoms and at least one nitrogen atom, the method comprising the steps of:

reacting an amine having a formula selected from $R^1R^2NH$ and $R^1NH_2$ wherein R¹ in the amine is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein R² in the amine is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group with a silicon source comprising at least one compound selected from the:

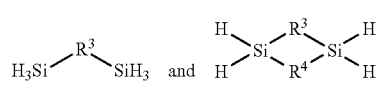

wherein R³ and R⁴ in the silicon source are independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group in the presence of a catalyst under reaction conditions sufficient for at least a portion of the silicon source and at least a portion of the amine to react and provide the organoaminosilane.

BRIEF DESCRIPTION OF FIGURE

FIG. 1 shows the relative deposition rates of the organoaminosilane described herein, 1-di-iso-propylamino-1,4-disilabutane, compared to deposition rates of other organoaminosilanes provided in reference articles such as bis (diethylamino)silane (BDEAS), bis(tert-butylamino)silane (BTBAS), bis(ethylmethylamino)silane (BEMAS), tris(dimethylamino)silane(TRDMAS), and di-sec-butylaminosilane (DSBAS).

DETAILED DESCRIPTION OF THE INVENTION

The organoaminosilanes described herein are used as precursors to form stoichiometric and non-stoichiometric silicon containing films such as, but not limited to, amorphous silicon, silicon-rich carbonitride, crystalline silicon, silicon oxide, silicon oxycarbide, silicon nitride, silicon oxynitride, and silicon oxycarbonitride. These precursors can also be used, for example, as dopants for metal containing films. The organoaminosilane precursors used in semi-conductor processes are typically high purity volatile liquid precursor chemical that are vaporized and delivered to a deposition chamber or reactor as a gas to deposit a silicon containing film via CVD or ALD processes for semiconductor devices. The selection of precursor materials for deposition depends upon the desired resultant silicon-containing material or film. For example, a precursor material may be chosen for its content of chemical elements, its stoichiometric ratios of the chemical elements, and/or the resultant silicon containing film or coating that are formed under CVD. The precursor material may also be chosen for various other characteristics such as cost, relatively low toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

The organoaminosilane precursors described herein exhibit a balance of reactivity and stability that makes them ideally suitable as CVD or ALD precursors in microelectronic device manufacturing processes. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor under a given vacuum to prevent condensation or particles from forming in the container, lines, or both. With regard to stability, other precursors may form silane ($SiH_4$) or disilane ($Si_2H_6$) as they degrade. Silane is pyrophoric at room temperature or it can spontaneously combust which presents safety and handling issues. Moreover, the formation of silane or disilane and other by-products decreases the purity level of the precursor and changes as small as 1-2% in chemical purity may be considered unacceptable for reliable semiconductor manufacture. In certain embodiments, the organoaminosilane precursors having Formulae A through E described herein comprise 2% or less by weight, or 1% or less by weight, or 0.5% or less by weight of by-product after being stored for a time period of 6 months or greater, or one year or greater which is indicative of being shelf stable. In addition to the foregoing advantages, in certain embodiments, such as for depositing a silicon oxide or silicon nitride or silicon film using an ALD, ALD-like, PEALD, or CCVD deposition method, the organoaminosilane precursor described herein may be able to deposit high density materials at relatively low deposition temperatures, e.g., 500° C. or less, or 400° C. or less, 300° C. or less, 200° C. or less, 100° C. or less, or 50° C. or less. In one particular embodiment, the organoaminosilane precursor can be used to deposit a silicon-containing film via ALD or PEALD at a temperature as low as 50° C. or less or at ambient or room temperature (e.g., 25° C.).

In one embodiment, described herein is a composition for forming a silicon-containing film comprising: an organoaminosilane having any one of Formulae A through E described herein and a solvent(s). Without being bound by any theory, it is believed that composition described herein may provide one or more advantages compared to pure organoaminosilane. These advantages include: better usage of the organoaminosilane in semiconductor processes, better stability over long term storage, cleaner evaporation by flash vaporization, and/or overall more stable direct liquid injection (DLI) chemical vapor deposition process. The weight percentage of the organoaminosilane in the composition can range from 1 to 99% with the balance being solvent(s) wherein the solvent(s) does not react with the organoaminosilane and has a boiling point similar to the organoaminosilane. With regard to the latter, the difference between the boiling points of the organoaminosilane and solvent(s) in the composition is 40° C. or less, more preferably 20° C. or less, or 10° C. or less. Exemplary solvents include, but not limited to, hexanes, octane, toluene, ethylcyclohexane, decane, dodecane, bis(2-dimethylaminoethyl) ether.

In one aspect, there is provided at least one organoaminosilane precursor a compound represented by one of following Formulae A through E below:

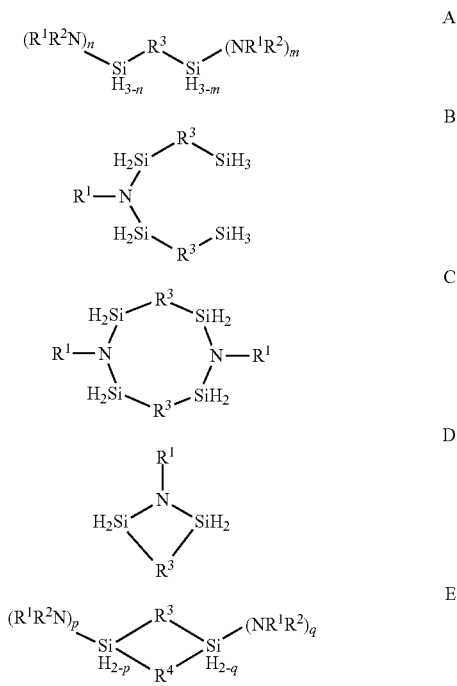

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom.

In the formulae and throughout the description, the term "alkyl" denotes a linear, or branched functional group having from 1 to 10 or 1 to 6 carbon atoms. Exemplary alkyl groups include, but are not limited to, methyl (Me), ethyl (Et), propyl (Pr$^n$), isopropyl (Pr$^i$), butyl (Bu$^n$), isobutyl (Bu$^i$), sec-butyl (Bu$^s$), tert-butyl (Bu$^t$), pentyl, iso-pentyl, tert-pentyl (Am$^t$), hexyl, iso-hexyl, and neo-hexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto. Exemplary organoaminosilanes having Formula A and having alkyl groups as $R^1$ and $R^2$ (if present) and an alkylene group such as methylene —CH$_2$— or ethylene —CH$_2$CH$_2$— as $R^3$ include, but are not limited to:

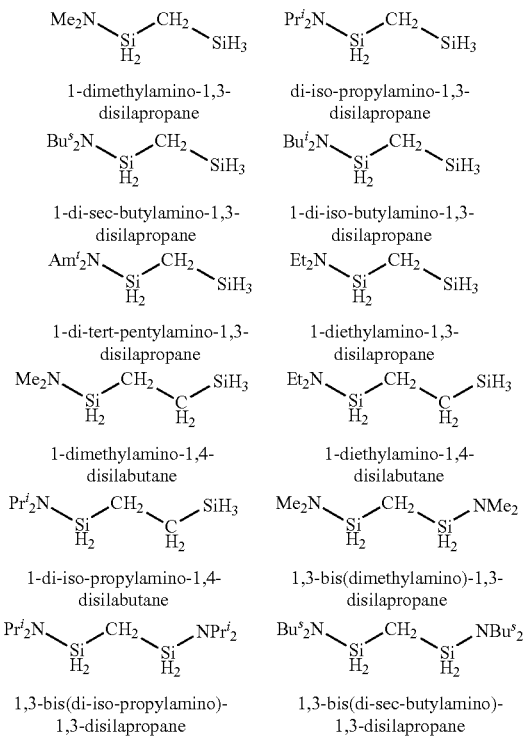

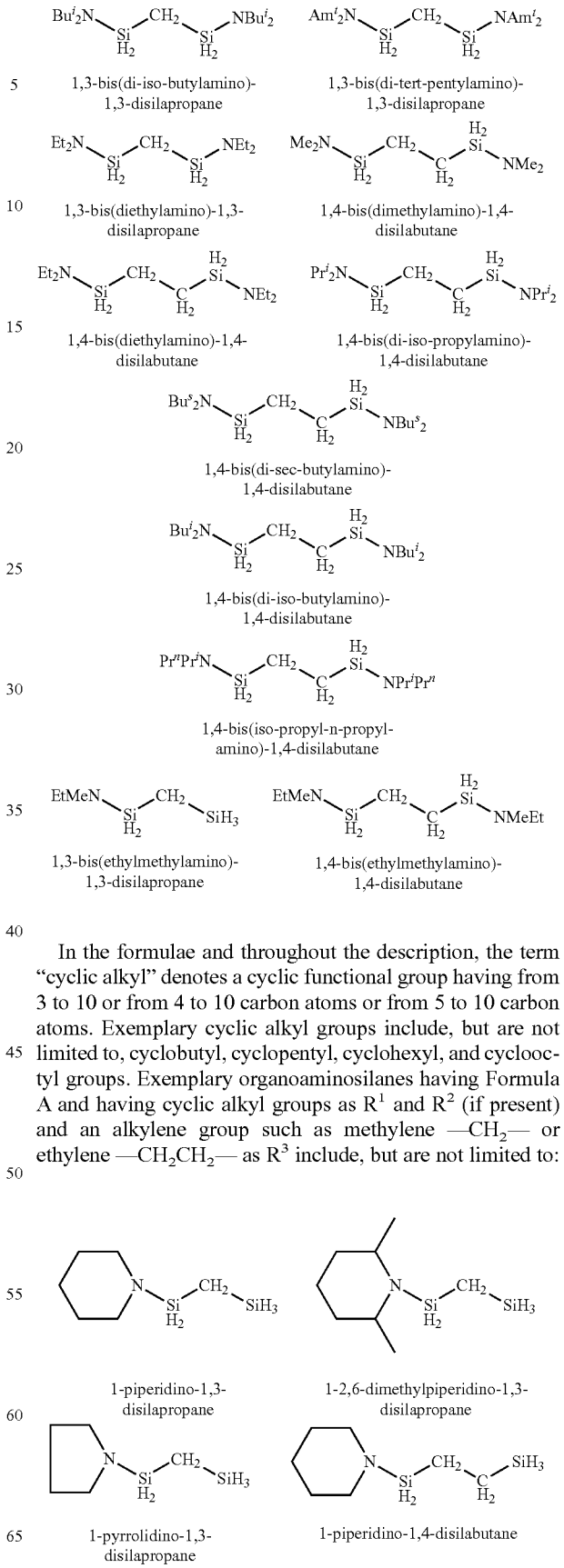

In the formulae and throughout the description, the term "cyclic alkyl" denotes a cyclic functional group having from 3 to 10 or from 4 to 10 carbon atoms or from 5 to 10 carbon atoms. Exemplary cyclic alkyl groups include, but are not limited to, cyclobutyl, cyclopentyl, cyclohexyl, and cyclooctyl groups. Exemplary organoaminosilanes having Formula A and having cyclic alkyl groups as $R^1$ and $R^2$ (if present) and an alkylene group such as methylene —CH$_2$— or ethylene —CH$_2$CH$_2$— as $R^3$ include, but are not limited to:

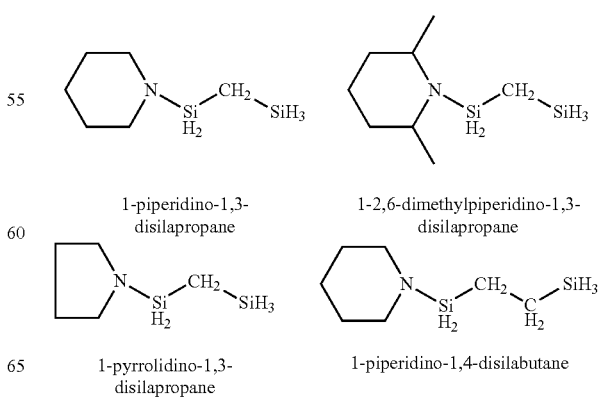

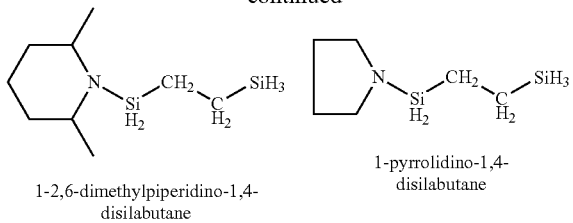

1-2,6-dimethylpiperidino-1,4-disilabutane 1-pyrrolidino-1,4-disilabutane

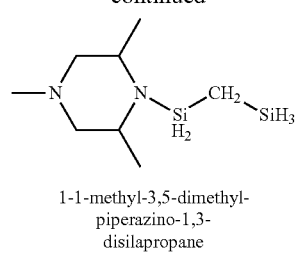

1-1-methyl-3,5-dimethyl-piperazino-1,3-disilapropane

In the formulae and throughout the description, the term "aryl" denotes an aromatic cyclic functional group having from 5 to 12 carbon atoms or from 6 to 10 carbon atoms.

Exemplary aryl groups include, but are not limited to, phenyl (Ph), benzyl, chlorobenzyl, tolyl, and o-xylyl. Exemplary organoaminosilanes having Formula A and having aryl groups as $R^1$ and $R^2$ (if present) and an alkylene group methylene —$CH_2$— or ethylene —$CH_2CH_2$— as $R^3$ include:

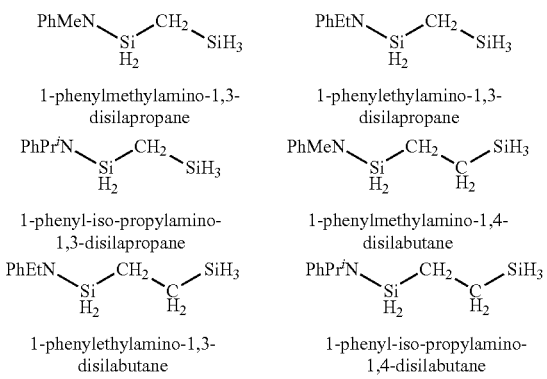

1-phenylmethylamino-1,3-disilapropane 1-phenylethylamino-1,3-disilapropane 1-phenyl-iso-propylamino-1,3-disilapropane 1-phenylmethylamino-1,4-disilabutane 1-phenylethylamino-1,3-disilabutane 1-phenyl-iso-propylamino-1,4-disilabutane In certain embodiments, one or more of the alkyl group, alkenyl group, alkynyl group, and/or aryl group in Formulae A through E may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, and/or aryl group in Formulae A through E may be unsubstituted.

In the formulae and throughout the description, the cyclic alkyl is substituted or is a hetero-cyclic alkyl group. The term "hetero-cyclic alkyl" denotes a cyclic functional group having from 3 to 10 or from 4 to 10 carbon atoms or from 5 to 10 carbon atoms as well as at least one oxygen atom or nitrogen atom or both. Exemplary organoaminosilanes having Formula A and having hetero-cyclic alkyl groups as $R^1$ and $R^2$ (if present) and an alkylene group methylene —$CH_2$— as $R^3$ include, but are not limited to:

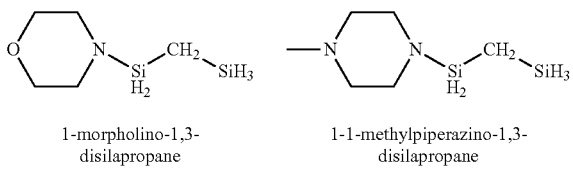

1-morpholino-1,3-disilapropane 1-1-methylpiperazino-1,3-disilapropane

In the formulae and throughout the description, the aryl is substituted or is a hetero-aryl group. The term "hetero aryl" denotes aryl functional group having from 3 to 10 or from 4 to 10 carbon atoms or from 5 to 10 carbon atoms as well as at least one oxygen atom or nitrogen atom or both. In the formulae and throughout the description, the term "alkenyl group" denotes a group which has one or more carbon-carbon double bonds and has from 3 to 10 or from 3 to 6 or from 3 to 4 carbon atoms.

In the formulae and throughout the description, the term "alkynyl group" denotes a group which has one or more carbon-carbon triple bonds and has from 3 to 10 or from 3 to 6 or from 3 to 4 carbon atoms.

In the formulae and throughout the description, the term "alkylene" denotes a hydrocarbon group having from 1 to 10 or from 4 to 10 carbon atoms or from 5 to 10 carbon atoms and are connected to two silicon atoms. Exemplary alkylene groups include, but are not limited to, methylene (—$CH_2$—), ethylene (—$CH_2CH_2$—), propylene (—$CH_2CH_2CH_2$—), and iso-propylene (—$CH(Me)CH_2$—).

In the formulae and throughout the description, the term "arylene" denotes an aromatic cyclic functional group having from 5 to 12 carbon atoms or from 6 to 10 carbon atoms, preferably the two Si atoms are bonded to 1,2-positions or 1,4-positions of the arylene groups.

In the formulae and throughout the description, the term "hetero-arylene" denotes an aromatic cyclic functional group having from 5 to 12 carbon atoms or from 6 to 10 carbon atoms, preferably the two Si atoms are bonded to 1,2-positions of the hetero-arylene groups.

In certain embodiments, $R^3$ can be linked in the Formula D to form a ring structure. Exemplary organoaminosilanes include, but are not limited to:

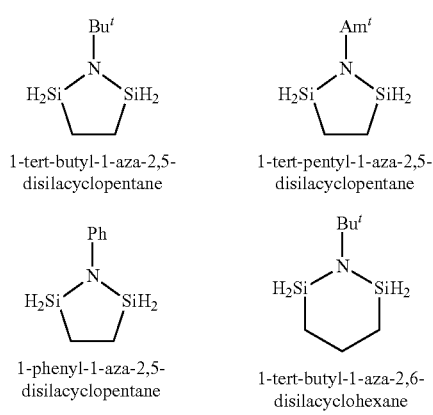

1-tert-butyl-1-aza-2,5-disilacyclopentane 1-tert-pentyl-1-aza-2,5-disilacyclopentane 1-phenyl-1-aza-2,5-disilacyclopentane 1-tert-butyl-1-aza-2,6-disilacyclohexane -continued

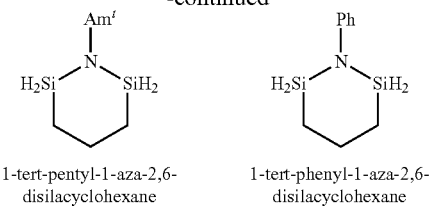

1-tert-pentyl-1-aza-2,6-disilacyclohexane 1-tert-phenyl-1-aza-2,6-disilacyclohexane In yet another embodiments, $R^3$ and $R^4$ are each methylene —$CH_2$— or, alternatively, each ethylene —$CH_2CH_2$— in Formula E. Exemplary organoaminosilanes include, but are not limited to:

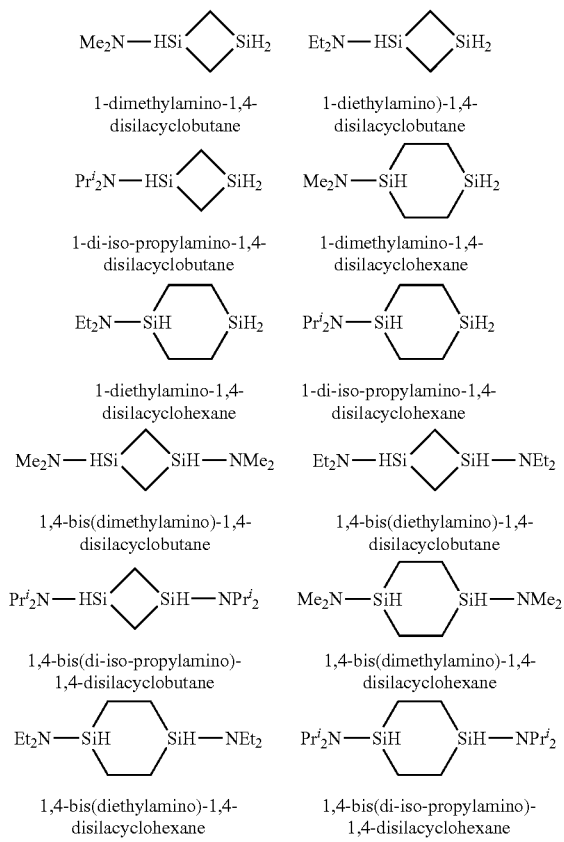

1-dimethylamino-1,4-disilacyclobutane 1-diethylamino-1,4-disilacyclobutane 1-di-iso-propylamino-1,4-disilacyclobutane 1-dimethylamino-1,4-disilacyclohexane 1-diethylamino-1,4-disilacyclohexane 1-di-iso-propylamino-1,4-disilacyclohexane 1,4-bis(dimethylamino)-1,4-disilacyclobutane 1,4-bis(diethylamino)-1,4-disilacyclobutane 1,4-bis(di-iso-propylamino)-1,4-disilacyclobutane 1,4-bis(dimethylamino)-1,4-disilacyclohexane 1,4-bis(diethylamino)-1,4-disilacyclohexane 1,4-bis(di-iso-propylamino)-1,4-disilacyclohexane The method used to form the silicon-containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon-containing film is deposited using an ALD process. In another embodiment, the silicon-containing film is deposited using a CCVD process. In a further embodiment, the silicon-containing film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the silicon-containing film. In one embodiment, the film is deposited via an ALD process by exposing the substrate surface alternatively to the one or more the silicon-containing precursor, oxygen-containing source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors other than the organoaminosilane precursor having the above Formulae A through E. Examples of additional silicon-containing precursors include, but are not limited to, monoaminosilane (e.g., di-iso-propylaminosilane, di-sec-butylaminosilane, phenylmethylaminosilane); organo-silicon compounds such as trisilylamine (TSA); siloxanes (e.g., hexamethyl disiloxane (HMDSO) and dimethyl siloxane (DMSO)); organosilanes (e.g., methylsilane, dimethylsilane, diethylsilane, vinyl trimethylsilane, trimethylsilane, tetramethylsilane, ethylsilane, disilylmethane, 2,4-disilapentane, 1,4-disilabutane, 2,5-disilahexane, 2,2-disilylpropane, 1,3,5-trisilacyclohexane and fluorinated derivatives of these compounds); phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or organoaminosilane precursor may be introduced into the reactor for a predetermined time period. In certain embodiments, the time period ranges from about 0.001 to about 500 seconds.

In certain embodiments, the silicon-containing films deposited using the methods described herein are formed in the presence of oxygen using an oxygen-containing source, reagent or precursor comprising oxygen. An oxygen-containing source may be introduced into the reactor in the form of at least one oxygen-containing source and/or may be present incidentally in the other precursors used in the deposition process. Suitable oxygen-containing source gases may include, for example, water ($H_2O$) (e.g., deionized water, purifier water, and/or distilled water), oxygen ($O_2$), oxygen plasma, ozone ($C_3$), NO, $N_2O$, $NO_2$, carbon monoxide (CO), carbon dioxide ($CO_2$), carbon dioxide plasma, and combinations thereof. In certain embodiments, the oxygen-containing source comprises an oxygen-containing source gas that is introduced into the reactor at a flow rate ranging from about 1 to about 2000 standard cubic centimeters (sccm) or from about 1 to about 1000 sccm. The oxygen-containing source can be introduced for a time that ranges from about 0.1 to about 100 seconds. In one particular embodiment, the oxygen-containing source comprises water having a temperature of 10° C. or greater. In embodiments wherein the film is deposited by an ALD or a cyclic CVD process, the precursor pulse can have a pulse duration that is greater than 0.01 seconds, and the oxygen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen-containing source or reagent is provided in a molecular amount less than a 1:1 ratio to the silicon precursor, so that at least some carbon is retained in the as deposited silicon-containing film.

In certain embodiments, the silicon-containing films comprise silicon and nitrogen. In these embodiments, the silicon-containing films deposited using the methods described herein are formed in the presence of nitrogen-containing source. A nitrogen-containing source may be introduced into the reactor in the form of at least one nitrogen-containing source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/argon plasma, nitrogen/helium plasma, nitrogen/hydrogen plasma, and mixture thereof. In certain embodiments, the nitrogen-containing source comprises an ammonia plasma or hydrogen/nitrogen plasma or nitrogen/argon plasma or nitrogen/helium plasma source gas that is introduced into the reactor at a flow rate ranging from about 1 to about 2000 standard cubic centimeters (sccm) or from about 1 to about 1000 sccm. The nitrogen-containing source can be introduced for a time that ranges from about 0.01 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), krypton (Kr), xenon (Xe), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen-containing source, the nitrogen-containing source, and/or other precursors, source gases, and/or reagents may be performed by changing the time for supplying them to change the stoichiometric composition of the resulting silicon-containing film.

Energy is applied to the at least one of the precursor, nitrogen-containing source, reducing agent, other precursors or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the precursor(s) having Formulae A through E is used in a composition comprising a solvent and an organoaminosilane precursor having Formulae A through E described herein, the solvent or mixture thereof selected does not react with the organoaminosilane. The amount of solvent by weight percentage in the composition ranges from 0.5% by weight to 99.5% or from 10% by weight to 75%. In this or other embodiments, the solvent has a boiling point (b.p.) similar to the b.p. of the organoaminosilane of Formulae A through E or the difference between the b.p. of the solvent and the b.p. of the organoaminosilane of Formulae A through E is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

In another embodiment, a vessel for depositing a silicon-containing film comprising one or more organoaminosilane precursor having Formulae A through E is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the organoaminosilane precursor having Formulae A through E is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the organoaminosilane precursor and/or other precursor can be maintained in separate vessels or in a single vessel having separation means for maintaining the organoaminosilane precursor and other precursor separate during storage.

In yet another embodiment, there is provided a method for preparing an organoaminosilane such as those having Formulae A through E described herein, wherein the method comprises the steps of:

reacting an amine having a formula which is either $R^1R^2NH$ or $R^1NH_2$ wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group and a silicon source which is at least one selected from compounds having the following structures:

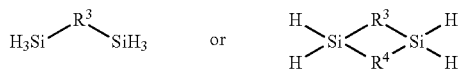

wherein $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group in the presence of a catalyst under reaction conditions sufficient for the silicon source and amine to react with or without an organic solvent and provide an organoaminosilane precursor comprising a compound represented by one of following Formulae A through E below:

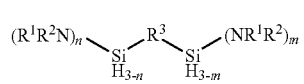

A

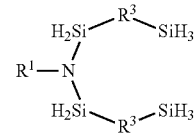

B

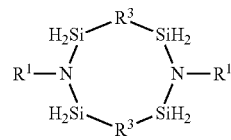

C

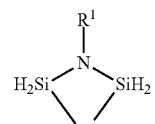

D

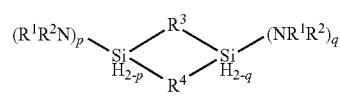

E wherein n in Formula A equals 1 or 2; m in Formula A equals 0, 1, 2, or 3; p and q equal 1 or 2 in Formula E and optionally wherein $R^3$ in Formula D forms a ring selected from a four-membered, five-membered or six-membered ring with the two silicon atoms and at least one nitrogen atom. Exemplary catalysts include, but not limited to, tris(pentafluorophenyl)borane, $BR_3$ (wherein R is selected from a linear, branched, or cyclic $C_1$ to $C_{10}$ alkyl group, a $C_5$ to $C_{10}$ aryl group, or a $C_1$ to $C_{10}$ alkoxy group), 1,3-diisopropyl-4,5-dimethylimidazol-2-ylidene, 2,2'-bipyridyl, phenanthroline, Mg[N(SiMe$_3$)$_2$]$_2$, [tris(4,4-dimethyl-2-oxazolinyl)phenylborate]MgMe, [tris(4,4-dimethyl-2-oxazolinyl)phenylborate]MgH, trimethylaluminium, triethylaluminum, aluminum chloride, Ca[N(SiMe$_3$)$_2$]$_2$, dibenzylcalcium, {CH—[CMeNC$_6$H$_3$-2,6-$^i$Pr$_2$]$_2$}CaH, triruthenium dodecacarbonyl, {CH—[CMeNC$_6$H$_3$-2,6-$^i$Pr$_2$]$_2$}Ca[N(SiMe$_3$)$_2$], bis(cyclopentadienyl)dialkyltitanium(IV), bis(cylopentadienyl)titanium(IV)difluoride, bis(cylopentadienyl)titanium(IV)dichloride bis(cylopentadienyl)titanium(IV)dihydride, TiMe$_2$(dmpe)$_2$ [dmpe=1,2-bis(dimethylphosphino) ethane], (C$_5$H$_5$)$_2$Ti(OAr)$_2$ [Ar=(2,6-(iPr)$_2$C$_6$H$_3$)], (C$_5$H$_5$)$_2$Ti(SiHRR')PMe$_3$ [wherein R, R' are each independently selected from a hydrogen atom (H), a methyl group (Me), and a phenyl (Ph) group], bis(benzene)chromium(0), chromium hexacarbonyl, dimanganese decacarbonyl, [Mn(CO)$_4$Br]$_2$, iron pentacarbonyl, (C$_5$H$_5$)Fe(CO)$_2$ Me, dicobalt octacarbonyl, nickel(II) acetate, nickel (II) chloride, [(dippe)Ni(μ-H)]$_2$ [dippe=1,2-bis(diisopropylphosphino) ethane], (R-indenyl)Ni(PR'$_3$)Me [wherein R is selected from 1-i-Pr, 1-SiMe$_3$, and 1,3-(SiMe$_3$)$_2$; wherein R' is selected from a methyl (Me) group and a phenyl (Ph) group], [{Ni(η-CH$_2$; CHSiMe$_2$)$_2$O}$_2${μ-(η-CH$_2$:CHSiMe$_2$)$_2$O}], nickel(II) acetylacetonate, ni(cyclooctadiene)$_2$, copper(II) fluoride, copper(I) chloride, copper(II) chloride, copper(I) bromide, copper(II) bromide, copper(I) iodide, copper(I) acetate, Cu(PPh$_3$)$_3$Cl, zinc chloride, [tris(4,4-dimethyl-2-oxazolinyl)phenylborate]ZnH, Sr[N(SiMe$_3$)$_2$]$_2$, Bis(cyclopentadienyl)dialkylzirconium (IV), Bis(cyclopentadienyl)zirconium(IV)difluoride, Bis(cylopentadienyl)zirconium(IV)dichloride, bis(cylopentadienyl)zirconium(IV)dihydride, [(Et$_3$P)Ru(2,6-dimesitylthiophenolate)][B[3,5-(CF$_3$)$_2$C$_6$H$_3$]$_4$], (C$_5$Me$_5$)Ru $(R_3P)_x(NCMe)_{3-x}]^+$ (wherein R is selected from a linear, branched, or cyclic $C_1$ to $C_{10}$ alkyl group and a $C_5$ to $C_{10}$ aryl group; x=0, 1, 2, 3), tris(triphenylphosphine) rhodium(I) carbonyl hydride, di-p-chloro-tetracarbonyldirhodium(I), tris(triphenylphosphine) rhodium(I) chloride (Wilkinson's Catalyst), hexarhodium hexadecacarbonyl, tris(triphenylphosphine)rhodium(I) carbonyl hydride, bis(triphenylphosphine)rhodium(I) carbonyl chloride, [RhCl(cyclooctadiene)]$_2$, tris(dibenzylideneacetone)dipalladium(0), tetrakis(triphenylphosphine)palladium(0), palladium(II) acetate, palladium(II) chloride, palladium(II) iodide, cesium carbonate, $(C_5H_5)_2SmH$, $(C_5Me_5)_2SmH$, $(NHC)Yb(N(SiMe_3)_2)_2$ [NHC=1,3-bis(2,4,6-trimethylphenyl)imidazol-2-ylidene)], tungsten hexacarbonyl, dirhenium decacarbonyl, triosmium dodecacarbonyl, tetrairidium dodecacarbonyl, (acetylacetonato) dicarbonyliridium(I), (POCOP)IrHCl [(POCOP)=2,6-$(R_2PO)_2C_6H_3$, (R is selected from isopropyl ($^i$Pr), normal butyl ($^n$Bu), and methyl (Me)], Ir(Me)$_2$(C$_5$Me$_5$)L [wherein L is selected from PMe$_3$ and PPh$_3$], [Ir(cyclooctadiene)OMe]$_2$, platinum(0)-1,3-divinyl-1,1,3,3-tetramethyldisiloxane (Karstedt's Catalyst), $H_2PtCl_6 \cdot nH_2O$ (chloroplatinic acid), bis(tri-tert-butylphosphine)platinum(0), PtO$_2$, and Pt(cyclooctadiene)$_2$.

In one embodiment of the method described herein, a cyclic deposition process such as CCVD, ALD, or PEALD may be employed, wherein at least one silicon-containing precursor selected from an organoaminosilane precursor having the formula described herein and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/argon plasma, nitrogen/helium plasma, nitrogen/hydrogen plasma, organic amines (e.g. methylamine, ethylamine, iso-propylamine, tert-butylamine), and/or a plasma derived from an organic amine are employed.

In certain embodiments, the gas lines connecting from the precursor canisters to the reaction chamber are heated to one or more temperatures depending upon the process requirements and the container of the organoaminosilane precursor having the formulae A through E described herein is kept at one or more temperatures for bubbling. In other embodiments, a solution comprising the at least one silicon-containing precursor having the formula described herein is injected into a vaporizer kept at one or more temperatures for direct liquid injection.

A flow of argon and/or other gas may be employed as a carrier gas to help deliver the vapor of the at least one organoaminosilane precursor to the reaction chamber during the precursor pulsing. In certain embodiments, the reaction chamber process pressure is about 10 torr or less, preferably about 1 torr.

In a typical ALD or CCVD process, a substrate such as, without limitation, a silicon oxide, carbon doped silicon oxide, flexible substrate, or metal nitride substrate is heated on a heater stage in a reaction chamber that is exposed to the silicon-containing precursor initially to allow the organoaminosilane to chemically adsorb onto the surface of the substrate. A purge gas such as nitrogen, argon, or other inert gas purges away unabsorbed excess organoaminosilane from the process chamber. After sufficient purging, an oxygen-containing source may be introduced into reaction chamber to react with the absorbed surface followed by another gas purge to remove reaction by-products from the chamber. The process cycle can be repeated to achieve the desired film thickness. In other embodiments, pumping under vacuum can be used to remove unabsorbed excess organoaminosilane from the process chamber, after sufficient evacuation under pumping, an oxygen-containing source may be introduced into reaction chamber to react with the absorbed surface followed by another pumping down purge to remove reaction by-products from the chamber. In yet another embodiment, the organoaminosilane and the oxygen-containing source can be co-flowed into reaction chamber to react on the substrate surface to deposit silicon oxide, carbon doped silicon oxide. In a certain embodiment of cyclic CVD, the purge step is not used.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon-containing film.

In another embodiment of the method disclosed herein, the films containing both silicon and nitrogen are formed using an ALD, PEALD, CCVD or PECCVD deposition method that comprises the steps of:

a. providing a substrate in an ALD reactor;
b. introducing into the ALD reactor at least one organoaminosilane precursor a compound represented by one of following Formulae A through E below:

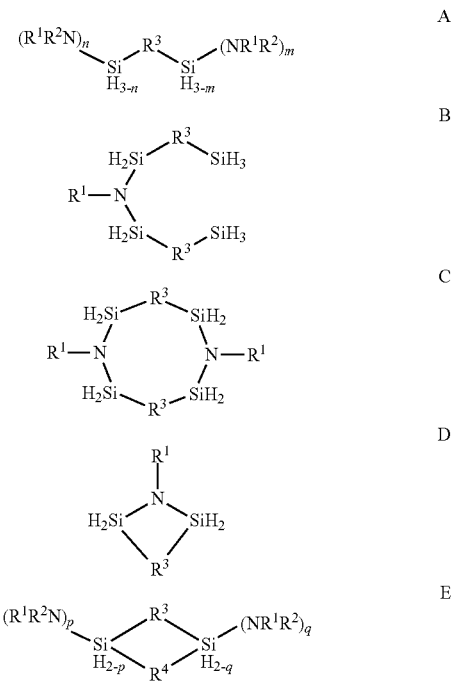

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;

c. chemisorbing the at least one organoaminosilane precursor onto a substrate;
    d. purging away the unreacted at least one organoaminosilane precursor using a purge gas;
    e. providing a nitrogen-containing source to the organoaminosilane precursor onto the heated substrate to react with the sorbed at least one organoaminosilane precursor; and
    f. optionally purging or pumping away any unreacted nitrogen-containing source.

In another aspect, there is provided a method of forming a film selected from a silicon oxide and a carbon doped silicon oxide film via a PEALD or a PECCVD deposition process, the method comprising the steps of:
    a. providing a substrate in a reactor;
    b. introducing into the reactor oxygen along with at least one organoaminosilane precursor a compound represented by one of following Formulae A through E below:

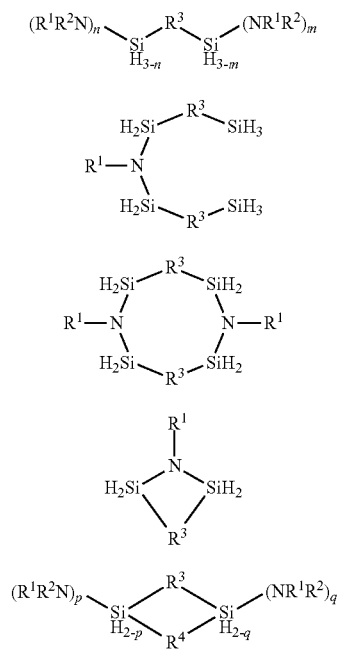

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;

c. purging the reactor with a purge gas along with oxygen;
    d. applying RF plasma;
    e. purging the reactor with a purge gas or pumping the reactor to remove unreacted organoaminosilane and any by-products; and wherein steps b through e are repeated until a desired thickness of the film is obtained.

In another embodiment of the method disclosed herein, the silicon-containing films is formed using a ALD deposition method that comprises the steps of:
    a. providing a substrate in a reactor;
    b. introducing into the reactor at least one organoaminosilane precursor a compound represented by one of following Formulae A through E below:

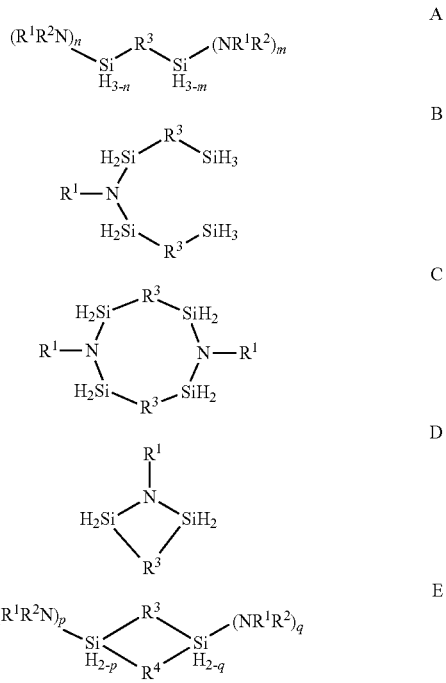

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; 1 and optionally wherein $R^3$ in Formula D forms a ring selected from a four-membered, five-membered or six-membered ring with the two silicon atoms and at least one nitrogen atom;

c. chemisorbing the at least one organoaminosilane precursor onto a substrate;

d. purging away the unreacted at least one organoaminosilane precursor using a purge gas;

e. providing an oxygen-containing source to the organoaminosilane precursor onto the heated substrate to react with the sorbed at least one organoaminosilane precursor; and f. optionally purging or pumping away any unreacted oxygen-containing source.

In another aspect, there is provided a method of forming a silicon nitride or silicon carbonitride film via PEALD or PECCVD process, the method comprising the steps of:

a. providing a substrate in a reactor;

b. introducing into the reactor a nitrogen-containing source and at least one organoaminosilane precursor a compound represented by one of following Formulae A through E below:

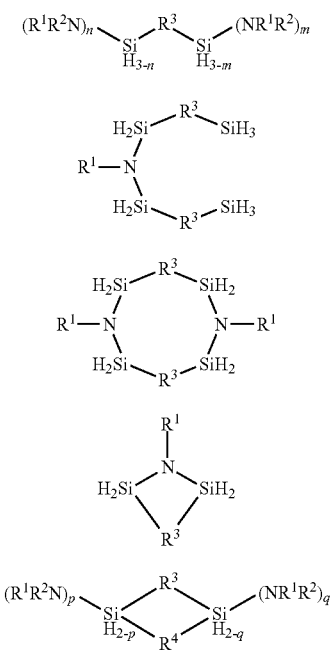

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;

c. purging the reactor with a purge gas along with the nitrogen-containing source;

d. applying RF plasma; and e. purging the reactor with a purge gas or pumping the reactor to remove unreacted organoaminosilane and any by-products; and wherein steps b through e are repeated until a desired thickness of the film is obtained.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

For multi-component silicon-containing films, other precursors such as silicon-containing precursors, nitrogen-containing precursors, reducing agents, or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one organoaminosilane precursor a compound represented by one of following Formulae A through E below:

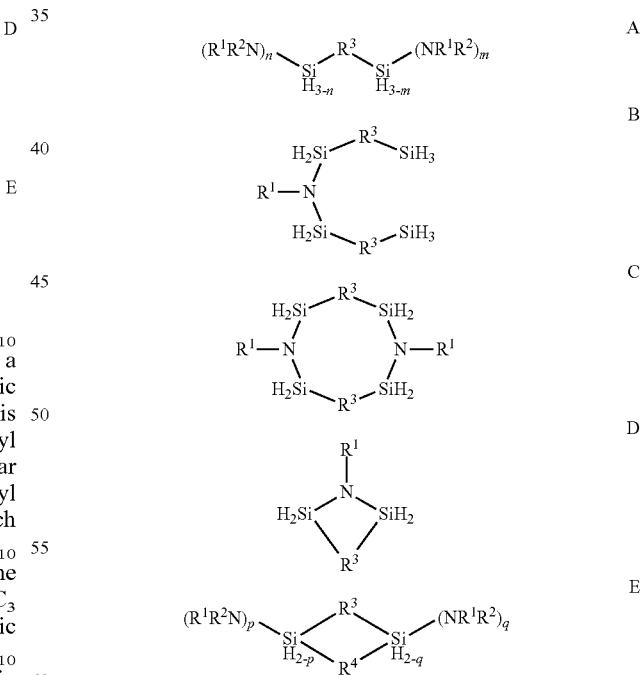

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and c. providing an oxygen-containing source into the reactor to at least partially react with the at least one organoaminosilane precursor and deposit a silicon-containing film onto the one or more substrates. In certain embodiments of the CVD method, the reactor is maintained at a pressure ranging from 10 mTorr to 760 Torr during the introducing step. The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

In a further embodiment of the method described herein, an amorphous or crystalline silicon film is deposited using the Formulae A through E precursor described herein. In this embodiment, the method comprises:

a. placing one or more substrates into a reactor which is heated to a one or more temperatures ranging from ambient temperature to about 700° C.;

b. introducing at least one organoaminosilane precursor a compound represented by one of following Formulae A through E below:

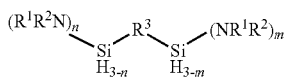

A

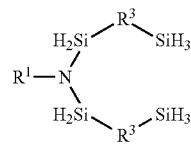

B

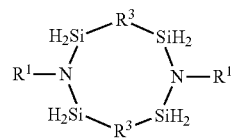

C

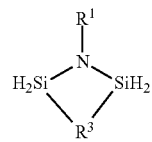

D

-continued

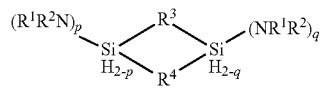

E wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and c. providing a reducing agent source into the reactor to at least partially react with the at least one organoaminosilane precursor and deposit a silicon-containing film onto the one or more substrates. The reducing agent is selected from the group consisting of hydrogen, hydrogen plasma, hydrogen chloride. In certain embodiments of the CVD method, the reactor is maintained at a pressure ranging from 10 mTorr to 760 Torr during the introducing step. The above steps define one cycle for the method described herein; and the cycle can be repeated until the desired thickness of a film is obtained.

For multi-component silicon-containing films, other precursors such as silicon-containing precursors, nitrogen-containing precursors, oxygen-containing sources, reducing agents, and/or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one organoaminosilane precursor a compound represented by one of following Formulae A through E below:

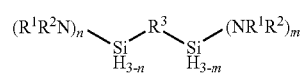

A

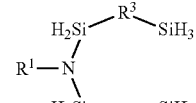

B

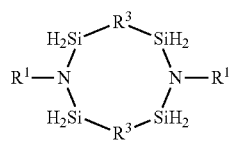

C

D

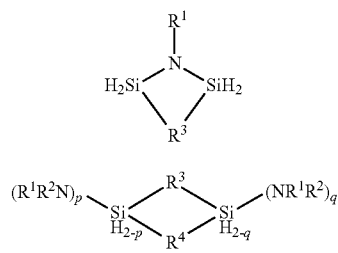

E

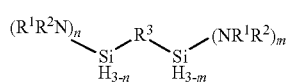

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom; and c. providing a nitrogen-containing source into the reactor to at least partially react with the at least one organoaminosilane precursor and deposit a silicon-containing film onto the one or more substrates. In certain embodiments of the CVD method, the reactor is maintained at a pressure ranging from 10 mTorr to 760 Torr during the introducing step.

In a further embodiment of the method described herein, the organoaminosilane precursors are used for depositing a silicon containing film which is an amorphous film, a crystalline silicon film, or a mixture thereof. In these embodiments, the silicon containing films is formed using a deposition method selected from ALD or cyclic CVD that comprises the steps of:

placing a substrates into a reactor which is heated to a temperature ranging from ambient temperature to about 700° C. and maintained at a pressure of 1 Torr or less;

introducing at least one organoaminosilane precursor a compound represented by one of following Formulae A through E below:

A

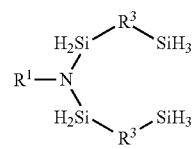

B

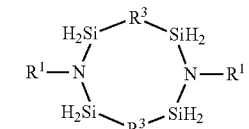

C

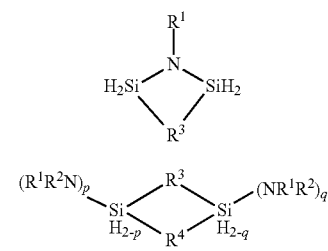

D

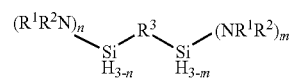

E

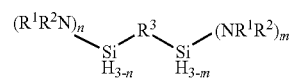

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein $R^2$ is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, $R^3$ and $R^4$ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein $R^3$ in Formula D forms a ring selected from a four-membered, five-membered or six-membered ring with the two silicon atoms and at least one nitrogen atom;

providing a reducing agent into the reactor to at least partially react with the at least one organoaminosilane precursor and deposit a silicon containing film onto the one or more substrates wherein the reducing agent is at least one selected from the group consisting of hydrogen, hydrogen plasma, or hydrogen chloride. The above steps define one cycle for the method described herein; and the cycle can be repeated until the desired thickness of a silicon containing film is obtained. The desired thickness of the film can range from 1 Å to 10,000 Å.

In another aspect, there is provided a method of forming a silicon-containing film onto at least a surface of a substrate using a deposition process selected from a plasma enhanced atomic layer (PEALD) process and a plasma enhanced cyclic chemical vapor deposition (PECCVD) process, the method comprising:

a. providing a substrate in an ALD reactor;

b. providing in the ALD reactor at least one organoaminosilane precursor comprising a compound represented by one of following Formulae A through E below:

A

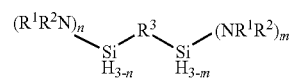

-continued

B

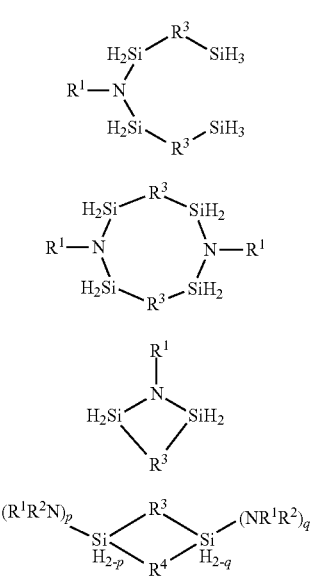

wherein R¹ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein R² is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, R³ and R⁴ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein R³ in Formula D forms a ring selected from a four-membered, five-membered or six-membered ring with the two silicon atoms and at least one nitrogen atom;

c. purging the ALD reactor with an inert gas;

d. providing a plasma source in the ALD reactor;

e. purging the ALD reactor with an inert gas; and wherein the steps b through e are repeated until a desired thickness of the silicon-containing film is obtained. The plasma source is selected from the group consisting of hydrogen plasma, argon plasma, helium plasma, neon plasma, xenon plasma, and mixtures thereof. The silicon-containing film is selected from the group consisting of silicon carbonitride, silicon carbide, silicon nitride, silicon carbonitride, and silicon carboxynitride.

In yet another aspect, there is provided a method of depositing amorphous or crystalline silicon film via an atomic layer deposition or cyclic chemical vapor deposition process or chemical vapor deposition at temperature lower than conventional silicon precursors, the method comprising the steps of:

a. providing a substrate in a reactor;

b. introducing into the reactor at least one organoaminosilane precursor a compound represented by one of following Formulae A through E below:

A
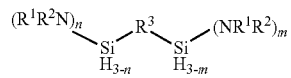

B
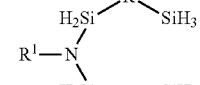

C

D
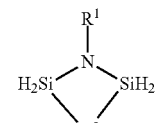

E
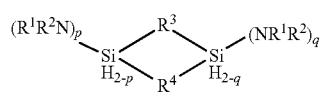

wherein R¹ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; wherein R² is selected from hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, R³ and R⁴ are each independently selected from a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1 or 2; m in Formula A equals 0, 1, 2, or 3; p and q in Formula E equal 1 or 2; and optionally wherein R³ in Formula D forms a ring selected from a four-membered, five-membered or six-membered ring with the two silicon atoms and at least one nitrogen atom;

c. purging the reactor with a purge gas wherein steps b through c are repeated until a desired thickness of the silicon film is obtained.

It is believed that Formulae A through E precursors can generate H₂Si: di-radicals or H₃Si. radical upon heating which can promote formation oligomers containing Si—Si bonds or anchor on the surface of a substrate. Those oligomers or anchored SiH₂ or SiH₃ can further form amorphous silicon films. In this or other embodiments, those oligomers function as a seed layer for subsequent deposition of silicon or silicon oxide films.

In certain embodiments, the organoaminosilane precursors having Formulae A through E described herein can also be used as a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino) hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino) tantalum (TBTDMT), tert-butylimino tri (ethylmethylamino)tantalum (TBTEMT), ethylimino tri (diethylamino)tantalum (EITDET), ethylimino tri (dimethylamino)tantalum (EITDMT), ethylimino tri (ethylmethylamino)tantalum (EITEMT), tert-amylimino tri (dimethylamino)tantalum (TAIMAT), tert-amylimino tri (diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino) bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the resultant silicon-containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon-containing films described herein have a dielectric constant of 6 or less. In these or other embodiments, the films can have a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon-containing film that is formed using the organoaminosilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to about 50%; and H ranges from about 0% to about 50% atomic percent weight % wherein x+y+z+v+w=100 atomic weight percent, as determined for example, by XPS or other means.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, a flexible substrate, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), light emitting diodes (LED), organic light emitting diodes (OLED), IGZO, and liquid crystal displays (LCD).

The following examples illustrate the method for preparing organoaminosilane precursors as well as depositing silicon-containing films described herein and are not intended to limit it in any way.

EXAMPLES

In the following examples, unless stated otherwise, properties were obtained from sample films that were deposited onto medium resistivity (8-12 Ωcm) single crystal silicon wafer substrates.

Example 1: Synthesis of
1-di-iso-propylamino-1,4-disilabutane

In a 3-necked round bottom flask equipped with a mechanic stirrer, a condenser, and an addition funnel, a solution of 1 equivalent 1,4-disilabutane in hexane was cooled to −20° C. with a cold bath. With stirring, a solution of 0.5 equivalent of lithium diisopropylamide in tetrahydrofuran (THF) was added dropwise through the addition funnel. After the addition was completed, the reaction mixture was allowed to warm up to room temperature. The reaction mixture was stirred at room temperature overnight, followed by filtration. A white precipitate, lithium hydride, formed from the reaction as a byproduct was filtered out. The solvent in the filtrate and excess 1,4-disilabutane was removed by distillation. The product, 1-di-iso-propylamino-1,4-disilabutane, was obtained by vacuum distillation. Gas chromatography (GC) showed that it was >98% pure 1-di-iso-propylamino-1,4-disilabutane. GC-MS showed the following peaks: 189 (M+), 188 (M−1), 174 (M−15), 159, 144, 130, 102.

Example 2: Synthesis of
1-t-butyl-1-aza-2-5-disilacyclopentane

In a 3-necked round bottom flask equipped with a mechanic stirrer, a condenser, and an addition funnel, a solution of 1 equivalent of 1,4-disilabutane in hexane was cooled to −20° C. with a cold bath. With stirring, a solution of 0.5 equivalent of lithium t-butylamide in THF was added dropwise through the addition funnel. After the addition was completed, the reaction mixture was allowed to warm up to room temperature. The reaction mixture was stirred at room temperature overnight, followed by filtration. A white precipitate, lithium hydride, formed from the reaction as a byproduct was filtered out. The solvent in the filtrate and the excess 1,4-disilabutane were removed by distillation. The product, 1-t-butyl-1-aza-2-5-disilacyclopentane, was obtained by vacuum distillation. Gas chromatography (GC) showed that it was >98% pure. GC-MS showed the following peaks: 159 (M+), 158 (M−1), 144 (M−15), 128, 114, 100.

Example 3: Synthesis of 1,4-bis(di-iso-propylamino)-1,4-disilabutane

In a 3-necked round bottom flask equipped with a mechanic stirrer, a condenser, and an addition funnel, a solution of 0.5 equivalent 1,4-disilabutane in hexane was cooled to −20° C. with a cold bath. With stirring, a solution of 1 equivalent of lithium di-iso-propylamide in THF was added dropwise through the addition funnel. After the addition was completed, the reaction mixture was allowed to warm up to room temperature. The reaction mixture was stirred at room temperature overnight, followed by filtration. A white precipitate, lithium hydride, formed from the reaction as a byproduct was filtered out. The solvent in the filtrate was removed by distillation. The product, 1,4-bis(di-iso-propylamino)-1,4-disilabutane, was obtained by vacuum distillation. B.P. 124° C./1 torr. GC-MS showed the following peaks: 288 (M+), 287 (M−1), 243, 229, 207, 188, 144, 130. $^1$H NMR: 4.59 (s, 4H), 3.03 (m, 4H), 1.08 (d, 24H), 0.73 (t, 4H). $^{13}$C NMR: 47.76, 24.42, 7.76.

Example 4: Synthesis of 1-diethylamino-1,4-disilabutane and 1,4-bis(diethylamino)-1,4-disilabutane In a scintillation vial, 2 equivalents 1,4-disilabutane and 1 equivalent diethylamine were combined. To this, 1 mol % of triruthenium dodecacarbonyl catalyst was added as a solution in THF, and the mixture was stirred overnight. The two major products observed in solution were 1-diethylamino-1,4-disilabutane and 1,4-bis(diethylamino)-1,4-disilabutane. GC-MS showed the following peaks: (a) 1-diethylamino-1,4-disilabutane: 161 (M+), 146 (M−15), 130, 116, 102, 89, 72; (b) 1,4-bis(diethylamino)-1,4-disilabutane: 232 (M+), 217 (M−15), 203, 187, 173, 160, 146, 130, 116.

Additional organoaminosilane precursors of Formula A to E were made via similar fashion as Examples 1 to 4 and were characterized by mass spectroscopy (MS). The molecular weight (MW), the structure, and corresponding major MS fragmentation peaks of each organoaminosilane precursor are provided in Table 1 to confirm their identification.

TABLE 1

Organoaminosilanes Having Formula A, B, C, D, and E.

| No. | Precursor Name | MW | Structure | MS Peaks |
|---|---|---|---|---|
| 1 | 1-dimethylamino-1,4-disilabutane | 133.34 | [structure] | 133, 116, 105, 86, 74, 58, 44 |
| 2 | 1,4-bis(dimethylamino)-1,4-disilabutane | 176.41 | [structure] | 176, 161, 145, 132, 116, 100, 89, 74 |
| 3 | 1-diethylamino-1,4-disilabutane | 161.41 | [structure] | 161, 146, 130, 116, 102, 89, 72 |
| 4 | 1,4-bis(diethylamino)-1,4-disilabutane | 232.52 | [structure] | 232, 217, 203, 187, 173, 160, 146, 130, 116 |
| 5 | 1-dipropylamino-1,4-disilabutane | 189.45 | [structure] | 189, 174, 161, 144, 131, 116, 100, 89 |
| 6 | 1,4-bis(dipropylamino)-1,4-disilabutane | 288.63 | [structure] | 288, 273, 260, 230, 189, 174, 161, 145, 128 |

TABLE 1-continued

Organoaminosilanes Having Formula A, B, C, D, and E.

| No. | Precursor Name | MW | Structure | MS Peaks |
|---|---|---|---|---|
| 7 | 1-di-iso-propylamino-1,4-disilabutane | 189.45 | 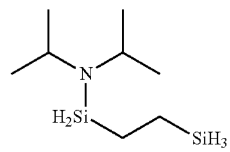 | 189, 188, 174, 159, 144, 130, 102 |
| 8 | 1,4-bis(di-iso-propylamino)-1,4-disilabutane | 288.63 | 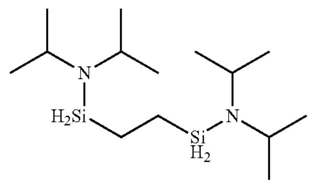 | 288, 287, 243, 229, 207, 188, 144, 130 |
| 9 | 1-(propyl-iso-propylamino)-1,4-disilabutane | 189.45 | 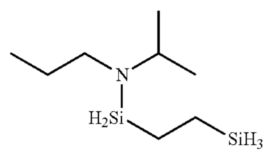 | 189, 174, 160, 144, 130, 116, 102, 86 |
| 10 | 1,4-bis(propyl-iso-propylamino)-1,4-disilabutane | 288.63 | 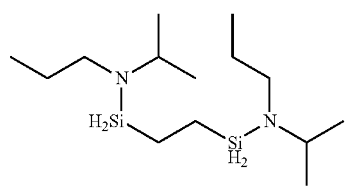 | 288, 274, 260, 244, 230, 216, 201, 188, 173, 160, 144, 128 |
| 11 | 1-dibutylamino-1,4-disilabutane | 217.50 | 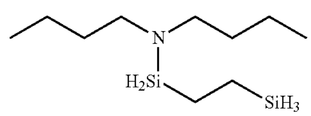 | 217, 202, 189, 175, 159, 145, 132, 116, 102, 89 |
| 12 | 1,4-bis(dibutylamino)-1,4-disilabutane | 344.73 | 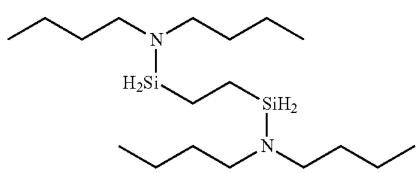 | 345, 330, 314, 302, 286, 217, 202, 175, 159, 116, 102 |
| 13 | 1-di-iso-butylamino-1,4-disilabutane | 217.50 | 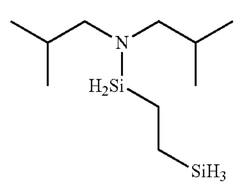 | 217, 202, 175, 159, 143, 116 |
| 14 | 1,4-bis(di-iso-butylamino)-1,4-disilabutane | 344.73 | 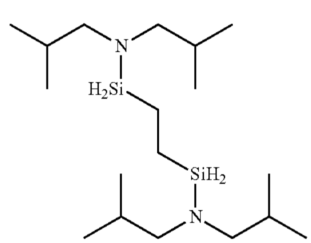 | 344, 329, 302, 286, 217, 202, 187, 175 |

TABLE 1-continued

Organoaminosilanes Having Formula A, B, C, D, and E.

| No. | Precursor Name | MW | Structure | MS Peaks |
|---|---|---|---|---|
| 15 | 1-di-sec-butylamino-1,4-disilabutane | 217.50 | 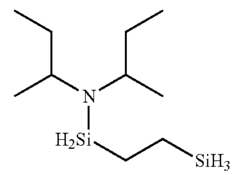 | 217, 202, 189, 172, 158, 144, 132, 114, 102 |
| 16 | 1-(sec-butyl-iso-propylamino)-1,4-disilabutane | 203.48 | 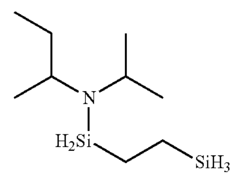 | 203, 188, 174, 158, 144, 130, 119, 102 |
| 17 | 1,4-bis(sec-butyl-iso-propylamino)-1,4-disilabutane | 316.68 | 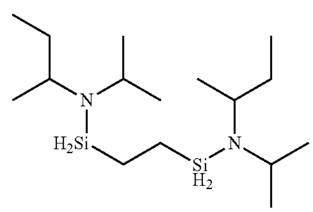 | 316, 301, 281, 257, 243, 229, 215, 202, 186, 172, 158 |
| 18 | 1-(dicyclohexylamino)-1,4-disilabutane | 269.58 | 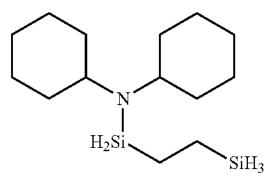 | 269, 254, 239, 227, 211, 199, 187, 129, 116 |
| 19 | 1-(cyclohexyl-iso-propylamino)-1,4-disilabutane | 229.51 | 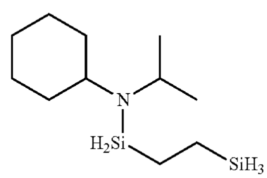 | 229, 214, 199, 187, 171, 159, 145, 131, 116, 102 |
| 20 | 1,4-bis(cyclohexyl-iso-propylamino)-1,4-disilabutane | 368.76 | 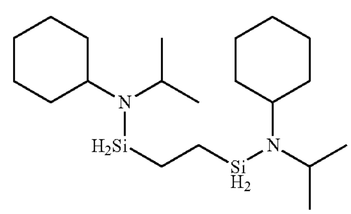 | 368, 353, 340, 327, 229, 185, 171, 159, 145, 130, 116 |
| 21 | 1-(2-pyridyl-methylamino)-1,4-disilabutane | 196.40 | 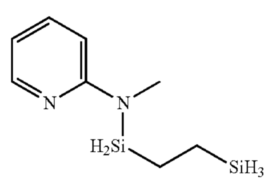 | 196, 181, 165, 151, 137, 121, 108 |
| 22 | 1,4-bis(2-pyridyl-methylamino)-1,4-disilabutane | 302.53 | 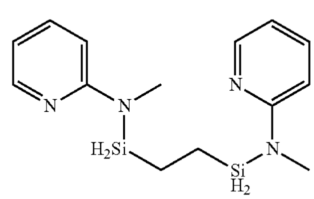 | 302, 287, 274, 258, 244, 223, 210, 196, 180, 166 |

TABLE 1-continued

Organoaminosilanes Having Formula A, B, C, D, and E.

| No. | Precursor Name | MW | Structure | MS Peaks |
|---|---|---|---|---|
| 23 | 1-pyrrolyl-1,4-disilabutane | 155.35 | 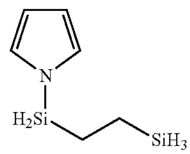 | 155, 140, 124, 112, 96, 86 |
| 24 | 1-(2,5-dimethylpyrrolyl)-1,4-disilabutane | 183.40 | 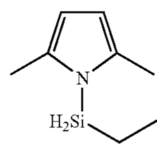 | 183, 168, 154, 136, 124, 110 |
| 25 | 1-(phenylmethylamino)-1,4-disilabutane | 195.41 | 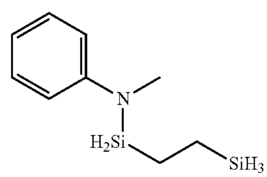 | 195, 180, 165, 149, 137, 119, 107, 193 |
| 26 | 1,4-bis(phenylmethylamino)-1,4-disilabutane | 300.55 | 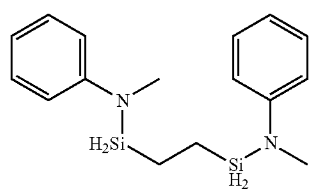 | 300, 285, 271, 255, 242, 226, 208, 193, 180, 165 |
| 27 | 1-(2-methylpiperidino)-1,4-disilabutane | 187.43 | 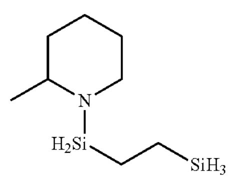 | 187, 172, 156, 141, 128, 113, 100, 84 |
| 28 | 1,4-bis(2-methylpiperidino)-1,4-disilabutane | 284.59 | 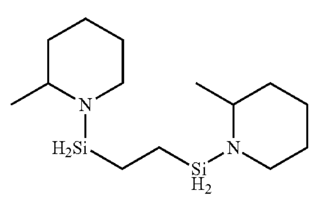 | 284, 269, 254, 240, 226, 208, 185, 173, 157, 143 |
| 29 | 1-(2,6-dimethylpiperidino)-1,4-disilabutane | 201.46 | 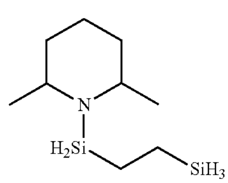 | 201, 186, 171, 155, 143, 130, 116, 102 |
| 30 | 1,4-dimethyl-1,4-diaza-5,8-disilacyclooctane | 174.39 | 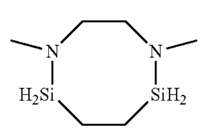 | 174, 160, 143, 130, 115, 100, 86, 72 |

TABLE 1-continued

Organoaminosilanes Having Formula A, B, C, D, and E.

| No. | Precursor Name | MW | Structure | MS Peaks |
|---|---|---|---|---|
| 31 | 1-(2,6-dimethylmorpholino)-1,4-disilabutane | 203.43 | 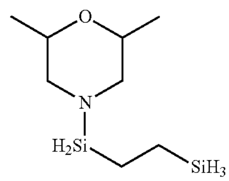 | 203, 188, 173, 161, 145, 130, 116, 102 |
| 32 | 1,4-bis(2,6-dimethylmorpholino)-1,4-disilabutane | 316.59 | 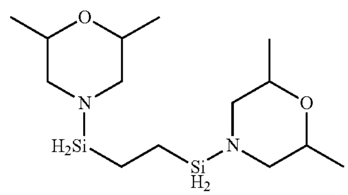 | 316, 301, 286, 274, 258, 244, 232, 216, 203, 188 |
| 33 | 1-(2-methylindolino)-1,4-disilabutane | 221.45 | 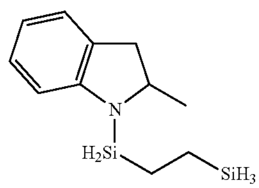 | 221, 206, 191, 176, 161, 146, 132, 117, 105 |
| 34 | 1,4-bis(2-methylindolino)-1,4-disilabutane | 352.63 | 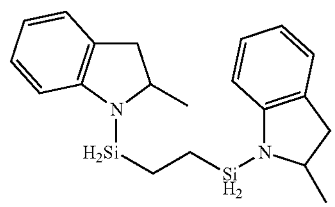 | 352, 337, 324, 308, 394, 280, 264, 250, 235, 221, 207, 191 |
| 35 | 1-iso-propylamino-1,4-disilabutane | 147.37 | 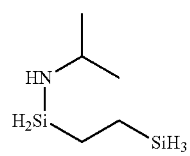 | 147, 132, 116, 100, 88, 72 |
| 36 | 1,4-bis(iso-propylamino)-1,4-disilabutane | 204.46 | 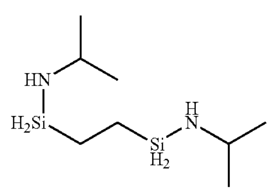 | 204, 189, 172, 160, 144, 130, 117, 102 |
| 37 | 1-iso-propyl-1-aza-2,5-disilacyclopentane | 145.35 | 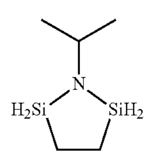 | 145, 130, 114, 100, 86 |
| 38 | 5-iso-propyl-5-aza-1,4,6,9-tetrasilanonane | 235.62 | 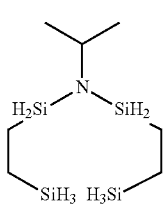 | 235, 220, 205, 191, 177, 159, 147, 130, 116, 102 |

TABLE 1-continued

Organoaminosilanes Having Formula A, B, C, D, and E.

| No. | Precursor Name | MW | Structure | MS Peaks |
|---|---|---|---|---|
| 39 | 1,6-di-iso-propyl-1,6-diaza-2,5,7,10-tetrasilacyclodecane | 290.70 | 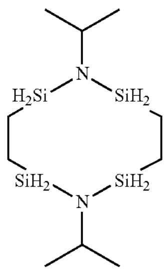 | 290, 275, 260, 246, 232, 218, 202, 190, 174, 159 |
| 40 | 1-tert-butyl-1-aza-2,5-disilacyclopentane | 159.38 | 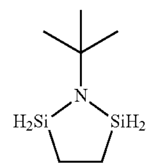 | 159, 158, 144, 128, 114, 100 |
| 41 | 5-tert-butyl-5-aza-1,4,6,9-tetrasilanonane | 249.65 | 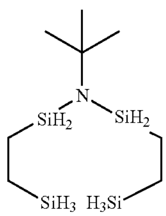 | 249, 234, 228, 215, 192, 176, 158, 144, 132, 117 |
| 42 | 1,6-di-tert-butyl-1,6-diaza-2,5,7,10-tetrasilacyclodecane | 318.76 | 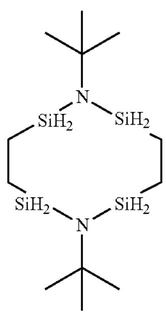 | 318, 303, 287, 271, 261, 247, 229, 213, 203, 187 |

Example 5: Atomic Layer Deposition of Silicon-containing Film using 1-di-iso-propylamino-1-4-disilabutane and Ozone The following depositions were performed on a laboratory scale ALD processing tool at two temperature conditions: 55° C. and 100° C. The silicon precursor was delivered to the chamber by vapor draw. All gases (e.g., purge and reactant gas or precursor and oxygen source) were preheated accordingly prior to entering the deposition zone. Gases and precursor flow rates were controlled with ALD diaphragm valves with high speed actuation. The substrates used in the deposition were 12-inch long silicon strips. A thermocouple attached on the sample holder to confirm substrate temperature during deposition. Depositions were performed using ozone (6-19% wt) as oxygen source gas.

A typical ALD cycle comprises the following steps:
a. providing a substrate in an ALD reactor;
b. providing in the ALD reactor at least one organoaminosilane precursor for 6 seconds
c. purging the ALD reactor with an inert gas for 6 seconds;
d. providing ozone in the ALD reactor for 4 seconds;
e. purging the ALD reactor with an inert gas for 6 seconds;

Steps b through e are repeated until a desired thickness of the film is obtained. Thickness and refractive indices of the films were measured using a FilmTek 2000SE ellipsometer by fitting the reflection data from the film to a pre-set physical model (e.g., the Lorentz Oscillator model). Wet etch rate was performed using 1% solution of 49% hydrofluoric (HF) acid in deionized water. Thermal oxide wafers were used as reference for each batch to confirm solution concentration. Typical thermal oxide wafer wet etch rate for 1% HF in $H_2O$ solution is 0.5 Å/s. Film thickness before and after etch was used to calculate wet etch rate. The thickness non-uniformity was calculated from 6-point measurements using the following equation: % non-uniformity=((max−min)/(2*mean)). Film elemental composition and density are characterized by X-Ray Photoelectron Spectroscopy (XPS). The growth rate (GPC) is determined by the thickness of the resultant film divided by total number of cycles.

TABLE 2

Process parameters, growth per cycle (GPC) and refractive index for silicon-containing film using 1-di-iso-propylamino-1-4-disilabutane and ozone

| Sample ID | Deposition Temperature (° C.) | Ozone concentration (% wt) | Growth Per Cycle (Å/cycle) | Refractive Index |
|---|---|---|---|---|
| Ex. Film 1 | 100 | 14 | 2.7 | 1.480 |
| Ex. Film 2 | 100 | 6 | 2.4 | 1.467 |
| Ex. Film 3 | 100 | 19 | 2.8 | 1.466 |
| Ex. Film 4 | 55 | 14 | 2.6 | 1.486 |
| Ex. Film 5[a] | 100 | 14 | 2.7 | 1.465 |

[a]Ex. Film 5 used a 60 second (s) evacuation time after the organoaminosilane precursor dose.

TABLE 3

Film composition measured by XPS for silicon-containing film using 1-di-iso-propylamino-1-4-disilabutane and ozone

| Sample ID | % O | % C | % Si | dHF WER (Å/s) |
|---|---|---|---|---|
| Ex. Film 1 | 67.6 | 0.8 | 32.1 | 3.3 |
| Ex. Film 2 | 62.2 | 5.0 | 32.7 | 1.9 |
| Ex. Film 3 | 66.8 | 1.0 | 32.2 | 4.1 |
| Ex. Film 4 | 55.0 | 9.6 | 33.3 | 1.6 |
| Ex. Film 5 | 66.5 | 0.9 | 32.6 | N/A |

FIG. 1 provides growth rate per cycle vs. temperature for the 1-di-isopropylamino-1,4,-disilabutane films (average value from Ex. Film 1, 3, 5 at 100° C.) and Ex. Film 4 as well as films deposited via a thermal ALD process using the following organoaminosilanes: bis(diethylamino)silane (BDEAS: I. Suzuki, K. Yanagita, and C. Dussarrat, ECS Trans. 3 (15), 119 (2007) and M. W. O'Neill, H. R. Bowen, A. Derecskei-Kovacs, K. S. Cuthill, B. Han and M. Xiao, Electrochemistry Society Interface Winter 2011, 33 (2011)), bis(tert-butylamino)silane (BTBAS: M. W. O'Neill, H. R. Bowen, A. Derecskei-Kovacs, K. S. Cuthill, B. Han and M. Xiao, Electrochemistry Society Interface Winter 2011, 33 (2011)), bis(ethylmethylamino)silane (BEMAS: S. J. Won, H-S. Jung, S. Suh, Y. J. Choi, N.-I. Lee, C. S. Hwang, H. J. Kim, J. Vac. Sci. Technol. A 30(1), 01 A126 (2012)), tris(dimethylamino)silane(TRDMAS: L. Han, and Z. Chen, Z. ECS Journal of Solid State Science and Technology 2(II): N228-N236 (2013)), di-sec-butylaminosilane (DSBAS: A. Mallikarjunan, A. Derecskei-kovacs, H. Chandra, B. Han, M. Xiao, X. Lei, M. L. O. Neill, H. Liang, H. Bo, Z. Qingfan, H. Cheng, 13th International Conference on Atomic Layer Deposition (2013)). As shown in FIG. 1, the silicon-containing films deposited using the organoaminosilanes described herein exhibited higher growth rates relative to the other, referenced organoaminosilane precursors. Further, the deposition temperature can be extended to one or more temperatures below 100° C., such as Ex. Film 4 which was deposited at a temperature of 55° C. Carbon concentration in the film range from 0.3 wt % to 9.6 wt % depending on the ozone concentration, suggesting it is possible to adjust the physical properties of the resultant silicon-containing films.

Example 6: Plasma Enhanced Atomic Layer Deposition of Silicon-containing Film using 1-di-iso-propylamino-1-4-disilabutane and Nitrogen/Argon Plasma A deposition of silicon containing film was performed using 1-di-iso-propylamino-1,4-disilabutane and a nitrogen/argon plasma. The silicon wafer was heated to 100° C. or 300° C., respectively. Deposition process was performed using 300 mm production tool, ASM Stellar 3000, repeated 1000 times, using the following process conditions:
 a. providing a substrate in an ALD reactor
 b. introducing organoaminosilane precursor: 1-di-iso-propylamino-1,4-disilabutane
  delivery conditions: Ar carrier gas 200 sccm, precursor container was kept at room temperature
  chamber pressure: 2 Torr
  precursor pulse: 1 second
 c. inert gas purge
  argon flow: 300 sccm
  chamber pressure: 2 Torr
  purge time: 5 seconds
 d. nitrogen/argon plasma
  argon flow: 500 sccm
  nitrogen flow: 200 sccm
  chamber pressure: 2 Torr
  plasma power: 500 W
  plasma time: 5 seconds
 e. purge plasma
  argon flow: 300 sccm
  chamber pressure: 2 Torr
  purge time: 0.5 seconds Deposition rate, refractive index, density as well as wet etch rate in dilute HF of the resultant films are listed below in Table 4. Referring to the data in Table 4, the oxygen is believed to come from post-deposition air exposure when samples were sending for XPS analysis.

TABLE 4

Deposition rate, refractive index of deposited films and film properties using 1-di-iso-propylamino-1-4-disilabutane and nitrogen/argon plasma

| Wafer temp (° C.) | Deposition Rate (Å/cycle) | Refractive index | C (%) | O content (%) | Density (g/cc) | WER in dHF (Å/s) |
|---|---|---|---|---|---|---|
| 100 | 0.41 | 1.73 | 9.6 | 16.3 | 2.0 | >33 |
| 300 | 0.15 | 2.02 | 4.9 | 2.4 | 2.9 | 0.8 |

Example 7: Plasma Enhanced Atomic Layer Deposition of Silicon-containing Film using 1-di-iso-propylamino-1-4-disilabutane and Argon Plasma A deposition of silicon containing film was performed using 1-di-iso-propylamino-1,4-disilabutane and argon plasma. The silicon wafer was heated to 100° C. or 300° C., respectively. Deposition process was performed using 300 mm production tool, ASM Stellar 3000, repeated 1000 times, using the following process conditions:
 a. providing a substrate in an ALD reactor
 b. introducing organoaminosilane precursor: 1-di-iso-propylamino-1,4-disilabutane
  delivery conditions: Ar carrier gas 200 sccm, precursor container was kept at room temperature
  chamber pressure: 2 Torr
  precursor pulse: 1 second
 c. inert gas purge
  argon flow: 300 sccm
  chamber pressure: 2 Torr
  purge time: 2 seconds d. argon plasma
   argon flow: 500 sccm
   chamber pressure: 2 Torr
   plasma power: 500 W
   plasma time: 5 seconds
e. purge plasma
   argon flow: 300 sccm
   chamber pressure: 2 Torr
   purge time: 2 seconds Deposition rate, refractive index, film composition, density as well as wet etch rate of the resultant films in dilute HF are listed below in Table 5. Referring to the data in Table 5, the oxygen is believed to come from post-deposition air exposure when samples were sending for XPS analysis.

TABLE 5

Deposition rate, refractive index of deposited films and film properties 1-di-iso-propylamino-1-4-disilabutane and argon plasma

| Wafer temp (° C.) | Deposition Rate (Å/cycle) | Refractive index | C (%) | O (%) | N (%) | Si (%) | Density (g/cc) | WER in dHF (Å/s) |
|---|---|---|---|---|---|---|---|---|
| 100 | 0.18 | 1.96 | 50.4 | 9.4 | 19.8 | 20.5 | 1.88 | <0.05 |
| 300 | 0.21 | 2.01 | 61.9 | 8.0 | 12.7 | 17.4 | 1.92 | <0.05 |

The wet etch rate in dilute HF of less than 0.05 Å/s, which is much lower than that of typical thermal oxide film (0.5 Å/s) under the same conditions, demonstrating the organo-aminosilanes described herein affect the resultant properties of the silicon-containing films deposited therefrom.

The invention claimed is:

1. A composition comprising at least one organoaminosilane compound represented by:

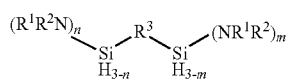

A wherein $R^1$ is selected from the group consisting of a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; $R^2$ is selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; $R^3$ are each independently selected from the group consisting of a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group; n in Formula A equals 1; m in Formula A equals 0; and, wherein the compound is made by a method comprising the steps of:
reacting an amine having a formula selected from $R^1R^2NH$ and $R^1NH_2$ wherein $R^1$ in the amine is selected from the group consisting of a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group; $R^2$ in the amine is selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, and a $C_5$ to $C_{10}$ aryl group, with a silicon source comprising at least one compound selected from the group consisting of

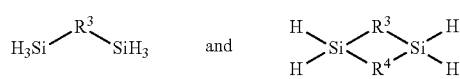

wherein $R^3$ and $R^4$ in the silicon source are independently selected from the group consisting of a linear or branched $C_1$ to $C_{10}$ alkylene group, a linear or branched $C_3$ to $C_6$ alkenylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, and a $C_5$ to $C_{10}$ hetero-arylene group in the presence of a catalyst under reaction conditions sufficient for at least a portion of the silicon source and at least a portion of the amine to react and provide the organoaminosilane, and wherein the organoaminosilane is greater than 98 wt. % pure.

2. The composition of claim 1 wherein the compound is free of halides.

3. The composition of claim 1 further comprising at least one member selected from the group consisting of nitrogen sources, oxygen sources, solvents, purge gases and reducing agents.

4. The composition of claim 1 wherein the compound is di-iso-propylamino-1,4-disilabutane.

5. The composition of claim 1 wherein the compound is at least one member selected from the group consisting of 1-dimethylamino-1,3-disilapropane, di-iso-propylamino-1,3-disilapropane, 1-di-sec-butylamino-1,3-disilapropane, 1-di-iso-butylamino-1,3-disilapropane, 1-di-tert-penty-lamino-1,3-disilapropane, 1-diethylamino-1,3-disilapropane, 1-piperidino-1,3-disilapropane, 1-2,6-dimethylpiperidino-1,3-disilapropane, 1-pyrrolidino-1,3-disilapropane, 1-dimethylamino-1,4-disilabutane, 1-dipropylamino-1,4-disilabutane, 1-di-iso-propylamino-1,4-disilabutane, 1-(propyl-iso-propylamino)-1,4-disilabutane, 1-dibutylamino-1,4-disilabutane, 1-di-iso-butylamino-1,4-disilabutane, 1-di-sec-butylamino-1,4-disilabutane, 1-(sec-butyl-iso-propylamino)-1,4-disilabutane, 1-(dicyclohexylamino)-1,4-disilabutane, 1-(cyclohexyl-iso-propylamino)-1,4-disilabutane, 1-(2-pyridyl-methylamino)-1,4-disilabutane, 1-pyrrolyl-1,4-disilabutane, 1-(2,5-dimethylpyrrolyl)-1,4-disilabutane, 1-(phenylmethylamino)-1,4-disilabutane, 1-(2-methylpiperidino)-1,4-disilabutane, 1-(2,6-dimethylpiperidino)-1,4-disilabutane, 1-(2,6-dimethylmorpholino)-1,4-disilabutane, 1-(2-methylindolino)-1,4-disilabutane, and 1-iso-propylamino-1,4-disilabutane.

* * * * *